United States Patent [19]
Park

[11] Patent Number: 4,596,470
[45] Date of Patent: Jun. 24, 1986

[54] THERMOCENTRIFUGOMETRIC ANALYSIS

[75] Inventor: Jin Y. Park, Moscow, Id.

[73] Assignee: Research Corporation, New York, N.Y.

[21] Appl. No.: 686,341

[22] Filed: Dec. 26, 1984

Related U.S. Application Data

[63] Continuation of Ser. No. 504,233, Jun. 14, 1983, abandoned.

[51] Int. Cl.$^4$ ............................................. G01N 25/00
[52] U.S. Cl. .................................... 374/14; 73/432 R
[58] Field of Search ........................ 73/432 R, 432 G; 374/14

[56] References Cited

U.S. PATENT DOCUMENTS

| | | |
|---|---|---|
| Re. 26,100 | 10/1966 | Cahn . |
| 2,515,056 | 7/1950 | Petit . |
| 2,609,617 | 9/1952 | Hall . |
| 2,814,944 | 12/1957 | Brown . |
| 2,826,079 | 3/1958 | Kuder et al. . |
| 2,882,717 | 4/1959 | Brown . |
| 2,907,117 | 10/1959 | Parkinson et al. . |
| 3,167,143 | 1/1965 | Savage . |
| 3,194,332 | 7/1965 | Wiedemann . |
| 3,292,417 | 12/1966 | Hayden et al. ........................ 374/14 |
| 3,717,210 | 2/1973 | Sieswerda . |
| 3,812,924 | 5/1974 | Fletcher et al. . |
| 3,813,928 | 6/1974 | Anderson . |
| 3,902,354 | 9/1975 | Harlan et al. ........................ 374/14 |
| 3,973,636 | 8/1976 | Uchida . |

OTHER PUBLICATIONS

C. J. Keattch, FRIC, An Introduction to Thermogravimetry Heyden & Sons, Ltd. 1969, pp. 8-10.
J. M. Smith, Chemical Engineering Kinetics, McGraw-Hill, 1981, pp. 535-537, 640-642.
O. Levenspiel, John Wiley & Sons, Inc. Chemical Reaction Engineering, 1972, pp. 485-487.

*Primary Examiner*—Stewart J. Levy
*Assistant Examiner*—Tom Noland
*Attorney, Agent, or Firm*—Scully, Scott, Murphy & Presser

[57] ABSTRACT

A method and four devices for measuring the change in mass of a sample subjected to selected temperatures and fluid variables is disclosed. The test sample is subjected to centrifugal force to apply the "apparent mass" of the sample by rotating the sample about a first axis of rotation. Any change in the mass of the test sample is then amplified by the centrifugal force and measured by the displacement of the sample about a second axis of rotation. The above method and four separate devices are disclosed. The first device balances the mass of the test sample against a known reference sample. The second device generates a counter-rotational force about the second axis to bring the sample to a "nulled" position. The third device balances the force generated about the second axis against a known and adjustable balance beam. A reciprocating means is used to couple the balance beam to a rotating sample holder. The fourth device generates a counter force along the balance beam to bring the sample to a "nulled" position. The devices are particularly adapted for mass change analysis in high temperature environments using high sweep gas rates and a variety of gaseous fluids.

49 Claims, 21 Drawing Figures

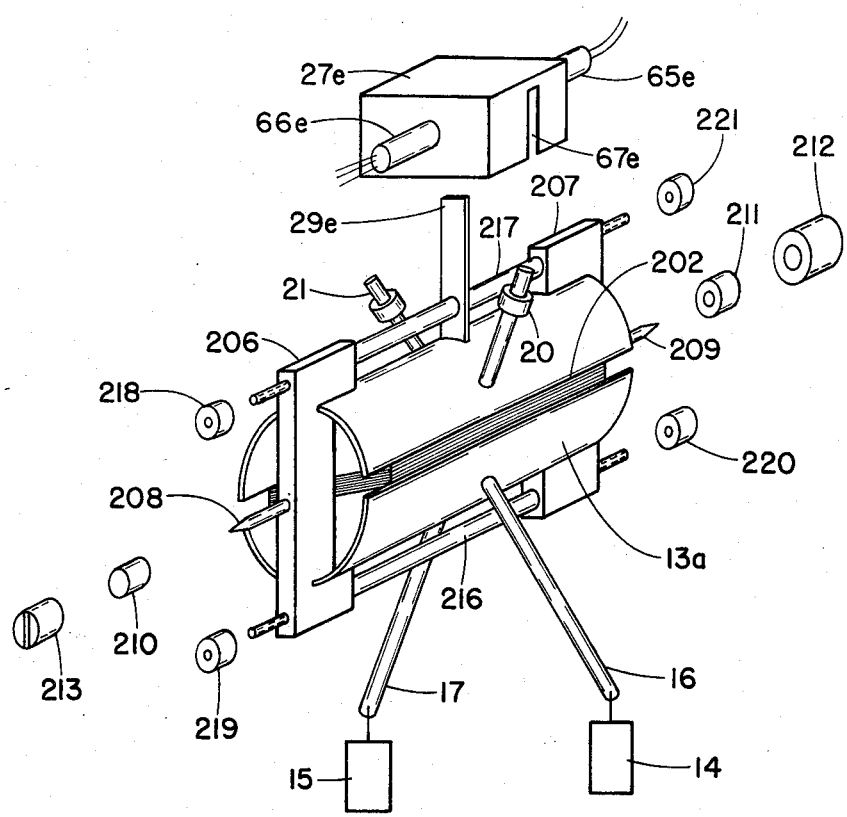
FIG.4
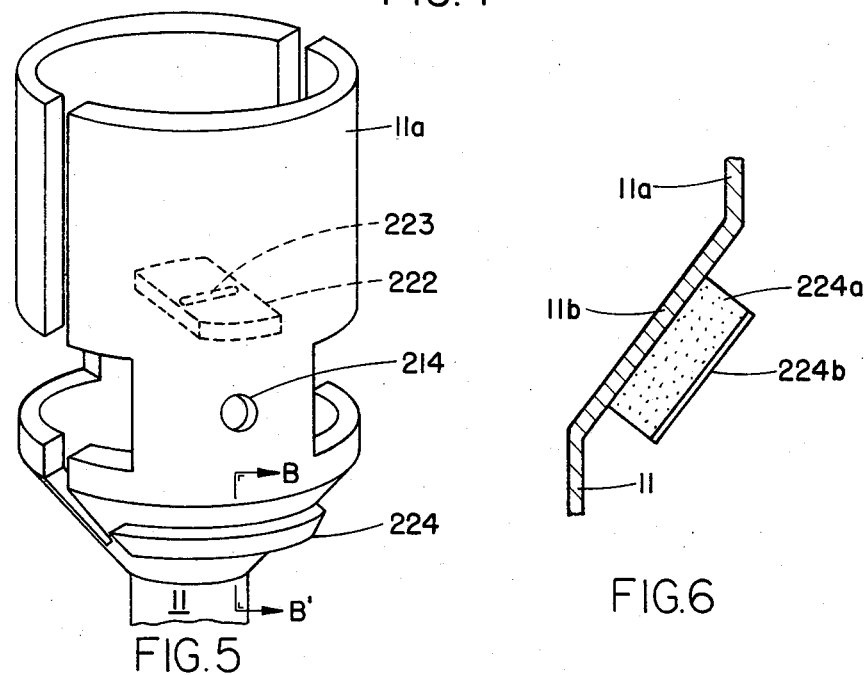
FIG.5
FIG.6

THERMOCENTRIFUGOMETRIC ANALYSIS

CROSS-REFERENCES TO RELATED APPLICATIONS

This application is a continuation of Ser. No. 504,233 filed June 14, 1983 and now abandoned. Reference is also made to applicants copending application Ser. No. 618,961, filed June 11, 1984.

BACKGROUND OF THE INVENTION

1. Field of the Invention

The present invention relates to a scientific instrument capable of performing conventional thermogravimetric analysis. The instrument is also capable of measuring the mass of an unknown sample in ambient atmosphere. Further, the invention provides a heretofore unknown method of measuring the continuous mass change of a solid subjected to high sweep gas velocities. Further, the invention will perform continuous mass change analysis with both high sweep gas velocities and elevated temperatures.

Conventional thermogravimetric analysis techniques are subject to fluctuating and unstable weight readings as the sweep gas flow past the solid being analyzed is increased. The fluctuations not only reduce the accuracy of measurement at low gas flow rates, but may also grow very rapidly, totally invalidating thermogravimetric analysis weight readings even at moderate sweep gas flow rates. J. M. Forgac and J. C. Angus, in "A Pressurized Thermobalance Apparatus For Use at Extreme Conditions," (Industrial and Engineering Chemistry Fundamentals, Volume 18, No. 4, Page 416 (1979)) reported that the weight reading became unstable due to a natural convection current induced by the temperature difference between the gas and the solid.

This instability severely limits the application of thermogravimetric analysis techniques in the kinetic study of fast gas-solid reactions at elevated pressures and temperatures because:

(a) a high sweep gas rate, required to enhance the contact between gas and solid and thereby determine the reaction kinetics (exclusive of external heat and mass transfer resistances) generates intense flow turbulences which cause instability of the solid;

(b) the flow turbulence generated increases as the gas is compressed to elevated pressures. The compressed gas then exerts an increased impact on the suspended solid;

(c) the temperature gradient developed about the solid generates a free convection current which adds to the flow turbulence.

The stability problems originate from the simple fact that gravity is a very weak force field and is easily disturbed by flow turbulences. It is generally considered unavoidable in conventional thermogravimetric analysis techniques.

The field of use for the present invention includes not only its application as a scientific instrument in the measurement of mass, but also in the duplication of measurements obtained in conventional thermogravimetric analysis. It also makes possible the measurement of the mass change of a solid subjected to high sweep gas velocities at elevated temperatures and pressures. Many industrially important gas-solid reactions are conducted at elevated pressures and temperatures such as those in coal gasification, coal combustion, oil shale retorting, dolomite sulfation, biomass pyrolysis, and mineral conversions.

Thermogravimetric analysis has rarely been used for liquid-solid contact systems because of the instability problems. The strong centrifugal force field of the present invention however makes possible the measurement of the mass and its change of a solid immersed in liquid. The present invention therefore also provides useful experimental means for the kinetic study of liquid-solid reactions such as those in coal liquification, leaching of minerals and ores, and purification of polluted water by activated carbon.

2. Discussion of the Prior Art

A conventional thermogravimetric analysis is disclosed in U.S. Pat. No. 3,973,636 which issued to Hiroshi Uchida on Aug. 10, 1976. This device is essentially a balance beam having a known reference material applied to one end of the balance beam and a test sample applied to the other end. The known reference material and the test sample are then subjected to high temperatures while any change in mass of the test sample is detected by an electromagnetic pickup device.

A general summary of thermogravimetric techniques may be found in "An Introduction to Thermogravimetry" by C. J. Keattch, FRIC published by Heyden and Son, Ltd. in cooperation with Sadtler Research Laboratories Inc., Page 1-14, 1969).

U.S. Pat. No. 3,812,924 to Fletcher et al. on May 28, 1974 discloses a device for monitoring a change in mass in varying environments. This device is a cantilever beam device using a strain gauge as the transducer for reflecting the change in mass of the sample.

The foregoing patents and the book excerpt describe conventional systems for thermogravimetric mass analysis. As discussed above, conventional systems are not capable of measuring the continuous mass change of a test solid under high sweep gas velocities.

The two most widely used laboratory reactors for fluid-solid reaction studies are described on pages 535 to 537 of the textbook entitled "Chemical Engineering Kinetics" 3rd Edition, authored by J. M. Smith, published by McGraw Hill Book Company in 1981. These reactors provide uniform fluid conditions and high fluid-solid contacting velocities. However, they are not capable of measuring the changing mass of the reacting solid. This textbook does describe on Page 640-642 a prior attempt to obtain uniform fluid conditions at high fluid-solid contacting velocities in conventional thermogravimetric analysis. This technique has had some success with extremely big and heavy single suspended capable of handling ordinary solid particles which are much smaller than one inch. The device illustrated, on page 641 (FIG. 14-2) is a stirred-tank single-pellet reactor used for the kinetic study of hydrofluorination of uranium dioxide.

Basket-type mixed reactors are also used in gas-solid contact systems. Such a device is disclosed in pages 485-487 of "Chemical Reaction Engineering", 2nd Edition by Octave Levenspiel, published by John Wiley and Sons, Inc. in 1972.

The fluid-solid contact devices disclosed above are not capable of measuring continuous mass changes in test samples under high sweep gas rate velocities. Even in the "stirred-tank single pellet reactor" the stirring speed is very restricted due to the stability limitation.

The present invention uses centrifugal force to amplify the apparent mass of the sample to be tested. In conventional thermogravimetric analysis, the weight of the sample is determined by the gravitational pull on the mass of the sample. In the present invention, the apparent mass of the sample is greatly amplified by centrifugal force.

U.S. Pat. No. 2,826,079 which issued to M. L. Kuder et al. on March 11, 1958 closes an automatic coin weighing machine which in FIG. 5 discloses a standard reference weight indicated by the numeral 4, and a coin to be sampled indicated by the numeral 5. If the coin is a counterfeit coin the difference in weight between the standard reference weight and the counterfeit coin will displace the center of mass slightly from the geometric center of the wheel. The apparatus then detects the displacement with an electronic mutual inductance micrometer. This patent teaches the concept of magnifying the apparent mass of the sample to be tested by nearly 500 times. This magnifies the small weight differential between the standard reference weight and the counterfeit coin 500 fold.

U.S. Pat. No. 2,814,944 to R. E. Brown issued on Dec. 3, 1957 discloses a centrifugal testing apparatus for instruments. This device has some structural similarities to the structures employed in one of the embodiments of applicant's invention. In this device, a pair of outwardly extending support arms rotate about a center axis. Each of the outwardly extending support arms carries a basket. One of the baskets is loaded with the instruments to be tested, the other basket is loaded with the appropriate counterweights to balance out the centrifuge. Dynamic unbalance above a predetermined tolerance is detected automatically and corrected by a servo-motor within the mechanism. If the dynamic imbalance is too high, the mechanism is shut down completely.

It should be noted that neither the Brown '944 patent nor the Kuter et al. '079 are capable of measuring a mass change in a coin or in the instrument. In addition, they are not capable of measuring a mass change under extreme thermal conditions, or under high sweep gas velocities and elevated temperatures and pressures.

SUMMARY OF THE INVENTION

The present invention discloses a process and several devices for measuring the change in mass of a test sample subjected to selected temperatures and fluid variables. The process includes the step of balancing the test sample against a known reactive force while the sample is suspended in an angularly displaceable sample receiving means. For each of the devices, the reactive force may be a known reference weight, or a null device which restores the angular rotation of the sample to a given null point. The sample receiving means is rotated about a first axis to amplify the apparent mass of the sample by centrifugal force. When the desired apparent amplification of the mass has been achieved, the test sample may be subjected to selective temperature and fluid variables. The invention then measures the change in angular displacement, or in the angular displacement force generated by the test sample as it is subjected to the centrifugal force and the selected temperature and fluid variables. The change in mass of the test sample may then be measured by a derivative value of the change in displacement force, or a change in its angular displacement.

In one embodiment of the invention, the centrifugometric mass analyzer includes a rotating shaft and two rotor arms for balancing a test sample against a standard reference material. After compensating for gravimetric balance between the sample and the reference material, the two rotor arms are rotated at high speed while the test sample is subjected to thermal analysis, or fluid-solid interchange. As the two rotor arms rotate, any imbalance in the mass in the test sample over the mass in the standard reference will cause the rotor disc to be angularly displaced. This displacement is a function of the difference in mass between the known standard and the mass of the test sample undergoing analysis. The angular displacement may be measured and calibrated through a variety of techniques.

In a second embodiment of the thermocentrifugometric analyzer, the angular displacement of the rotor is opposed by a null motor apparatus which senses the angular displacement of the rotor and generates a counter-reactive force to restore it to its original position. The amount of reactive force necessary to maintain the rotor at the null point is then used to measure the mass of the test sample.

In a third embodiment of the present invention one or more rotor arms are provided which are biased against a balance beam positioned over a reciprocating rod connected to the rotor arm. Means are provided for calibrating the balance beam to provide a known reactive force for the sample as it is subjected to centrifugal force. After the first reference value is generated by the balance beam, any change in mass in the test sample will be measured directly by a change in the balance beam position as the test sample undergoes analysis.

A fourth embodiment of the present invention represents the null balance operation mode of the third embodiment. The vertical displacement of the reciprocating rod is opposed by a null balance device which senses the vertical displacement and generates a counter-reactive force to restore it to its original position. The amount of reactive force to maintain the piston at the null point is then used to measure the mass of the tested sample.

The present invention provides a thermocentrifugometric analysis as opposed to the previously known thermogravimetric analysis. The thermocentrifugometric analysis rotates the solid at high speeds, in which the high-speed rotation not only provides very efficient interchange between the gas and solid, but also generates a very strong and stable centrifugal force field under which the changing mass of the rotating solid can be continuously measured. Since the centrifugal force field is several orders of magnitude greater than gravitational force, the measurement is extremely stable and not affected by gas-solid flow disturbances.

Moreover, the present invention provides for the amplification of the gravitational force field by centrifugal force. A 5 cm long arm rotating at 2000 rpm will provide a 224 fold increase in the mass change of the sample to be tested. By varying the speed of the rotation, there may be varied the amount of centrifugal force applied to the test sample. Thus the degree of amplification of the change in mass may be varied to accommodate various fluid-solid reactions.

The present invention provides an extremely accurate mass measurement device that will reflect a change in mass at the nano gram level of mass change.

It is therefore an object of the present invention to provide a novel method of measuring the change in mass of a test sample by rotating the sample about a first axis to subject the sample to centrifugal force to amplify any change in the "apparent mass" of the test sample.

It is another object of the present invention to provide a method and several means for detecting the change in the "apparent mass", by measuring rotational force generated by test sample about a second axis of rotation.

It is another object of the present invention to provide a method and several test instruments that will measure the change in mass at a high temperature and a variety of fluid conditions.

It is another object of the present invention to provide a centrifugometric mass analysis device that is capable of providing stable and continuous mass change readings when the test sample is subjected to elevated temperatures and pressures.

A further object of the present invention is to provide an instrument that will indicate continuous mass change readings when a material to be tested is subjected to elevated temperatures and pressures wherein the fluid is coacting with the solid at a high sweep fluid velocity. The high speed rotation provides a relative velocity of 10 meters per second within a pressurized and heated autoclave when a 5 cm arm is used while rotating at 2000 rpm.

The present invention also provides a mass measurement device to determine the mass of any unknown sample by comparing it to a known reference material while subjecting the test material and the reference material to a strong and stable centrifugal force.

The present invention also provides a mass measurement device to determine the mass of any unknown sample by comparing it to a known and adjustable force while subjecting the test material to a strong and stable centrifugal force.

BRIEF DESCRIPTION OF THE DRAWINGS

The foregoing objects and advantages of the centrifugometric mass analyzer may be more readily understood by one skilled in the art with reference being had to the following detailed description of the several preferred embodiments thereof, taken in conjunction with the accompanying drawings wherein like elements are designated by identical reference numerals throughout the several views, in which:

FIG. 4 is an exploded isometric view of a portion of the null motor device illustrated in FIG. 3.

FIG. 5 is an isometric view of another portion of the null motor embodiment illustrated in FIG. 3.

FIG. 6 is a cross-sectional view of a radiation reflector wherein the cross-section is taken along section line B-B' illustrated in FIG. 5.

DETAILED DESCRIPTION

Figure 1:
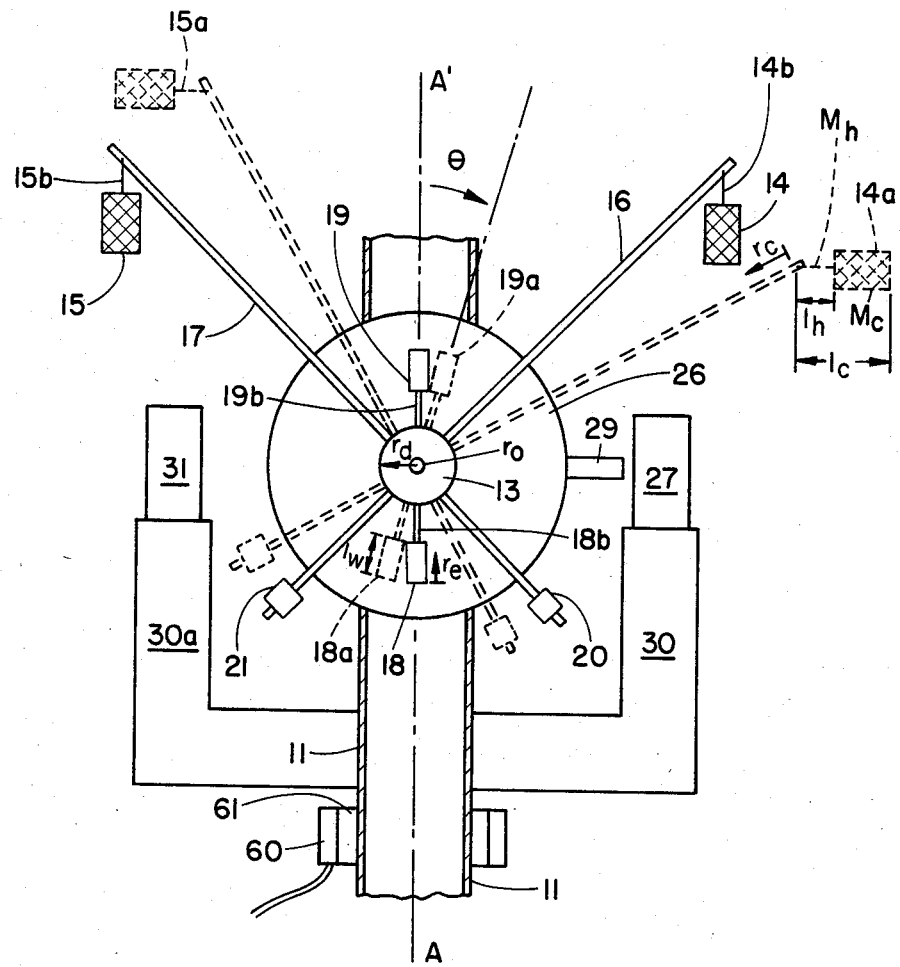
FIG. 1 is a partially cross-sectioned and front view of the angularly displaceable embodiment of the present invention illustrated in a static state through solid lines, and in a dynamic state through dotted lines.

The present invention relates to a process and several forms of mechanical apparatus for carrying out the process when it is desired to determine the change in mass of a test sample when the test sample is subjected to selected temperature and fluid variables. In conducting the process, the test sample is balanced against a known reactive force and suspended in an angularly displaceable receiver. The known reactive force, as will be hereinafter described with respect to the several mechanical embodiments of the invention, may include a known reference weight, a null motor, a balance beam, or a combination of these.

In measuring the change in mass, the sample and its receiver are rotated about a first axis to amplify the apparent mass of the sample by centrifugal force. Thus if the initial mass of the sample were one gram, and the reference weight were one gram, the apparent mass may be amplified to 100 grams by selecting an appropriate speed of rotation, and placing the sample receiving means at an appropriate distance from the rotating axis. Both the speed of rotation, and the radius of the circle traversed by the sample may be varied to alter the apparent mass of the sample. If the apparent mass were amplified by 1000 times, a relatively small differential change in the mass of the test sample may be easily determined by measuring the angular displacement of the sample as it rotates about a second axis. In an alternate embodiment of the invention, this angular displacement about a second axis is balanced by means of a null motor. In other alternate embodiments of the invention, the angular displacement is first converted to a vertical displacement of a reciprocating piston placed along the first axis of rotation. The vertical displacement is measured in a third embodiment, and it is balanced by means of a measurable counter-reactive force in a fourth embodiment.

While the device will measure mass by comparing an unknown sample with a known reference material or force, it is particularly suited for measuring the change in mass when a test sample is subjected to one or more of the following variables:

(a) a selected temperature or series of temperatures substantially above or below the ambient atmospheric temperature;

(b) a selected atmospheric pressure or series of atmospheric pressures above or below ambient atmospheric pressure;

(c) a specific fluid-solid reaction wherein a preselected test sample is rotated in a fluid or chamber containing the reactant fluid;

(d) a selected high sweep fluid velocity or a series of high sweep fluid velocities.

The sweep fluid velocities may be altered by a plurality of means, such as the configuration of the sample container, the speed at which the sample is rotated about its first axis of rotation, the radius the circular path defined by the sample, baffling and recirculation means to agitate the gas within a test chamber, and external means for directing a high sweep gas flow into the chamber to impinge upon the rotating test sample.

The amplification of apparent mass as indicated above is dependent upon the radius of the circle defined by the test sample as it rotates, and the speed of rotation. The following table sets forth the apparent amplification of the mass at various radii of circular motion and rotational speeds.

| RPM Of Test Sample | 5 cm Arm Length | 7.5 cm Arm Length |
| --- | --- | --- |
| 500 | 14 times $M_s$ | 21 times $M_s$ |
| 1000 | 56 times $M_s$ | 84 times $M_s$ |
| 2000 | 224 times $M_s$ | 336 times $M_s$ |
| 4000 | 896 times $M_s$ | 1344 times $M_s$ |
| 5000 | 1400 times $M_s$ | 2100 times $M_s$ |

The arm length described above is the radius of the circle defined by the test sample.

While the amplification of mass by centrifugal force is a well-known principle of physics, it not heretofore been applied to the field of thermogravimetric mass analysis. As indicated previously, at extremely elevated temperatures thermoconvection currents generated by the difference in temperatures between the test sample and the reactive gas may render a conventional thermogravimetric mass analysis reading inaccurate. The present invention provides a means of amplifying the change in the gravimetric mass by a factor of several hundred fold to assist in measuring the change as it occurs through a change in temperature, a change in sweep fluid velocity, a change in gas pressure, or a change in gas composition.

As indicated previously, the process of the present invention may be practiced with at least four different mechanical structures. These structures may be generally described by:

(a) angular displacement apparatus;
(b) null motor apparatus;
(c) reciprocating shaft displacement apparatus
(d) reciprocating shaft null balance apparatus.

The angular displacement apparatus may be summarized as a centrifugometric mass analyzer for measuring the continuous mass change of a test material subjected to selected temperatures and other fluid variables. The apparatus has a pair of angularly displaceable arms with a sample receiving means located at the end of one arm, and a known reference material receiving means located at the end of the other arm. The arms are balanced for rotation about a second axis of rotation. After initial balancing of the test sample with one or more known reference weights, the device is then spun or rotated about a first axis of rotation to subject the test sample to centrifugal force. Any change in the mass of the test sample then results in rotation of the pair of arms about the second axis of rotation. This angular displacement is then measured. The change in mass of the tested material may then be determined by a derivative value of the change of angular rotation. A variety of methods and means may be provided for measuring the angular displacement of the rotating arms.

The null motor apparatus may be differentiated from the angular displacement apparatus inasmuch as a null motor is connected to the support means for the two rotating arms. The null motor spins on the first axis of rotation with the pair of rotating arms, and any change in angular displacement about the second axis of rotation is immediately sensed by the null motor apparatus and a counter force or reactive force is generated to neutralize the angle of rotation and restore it to a center "nulled" position. The mass of the tested material and its change may then be determined by measuring the counter rotational force applied by the null motor to the angularly displaceable arms and its derivative value.

The reciprocating piston displacement apparatus may be distinguished from the above devices inasmuch as a single angularly displaceable arm is provided for rotation about a first axis. A known and adjustable reference force is provided on the reciprocating piston placed along the first rotational axis and the angular displacement of the rotating arm and the tested solid exert a compressive or extensive force on the piston. A measurement means is used to measure the vertical displacement of the piston caused by the difference between the reference force and the force generated by the rotating arm and the tested solid. The displacement is then used to determine the mass of the tested solid by means of a calibration formula established prior to the operation through a series of mass measurements on various reference weights of known mass. A derivative value of the displacement is used to determine the corresponding derivative value of the change in mass as the tested solid is subjected to preselected temperature and fluid conditions.

The reciprocating piston null balance apparatus may be distinguished from the above reciprocating piston displacement apparatus inasmuch as a null device is connected to the reciprocating piston. The vertical displacement of the reciprocating piston is immediately sensed by the null device and a reactive force is generated to neutralize the displacement and restore it to its original null position. The mass of the tested solid and its change may then be determined by measuring the reactive force applied by the null device on the piston and its derivative value.

DETAILED DESCRIPTION OF THE ANGULAR DISPLACEMENT APPARATUS

Figure 13:
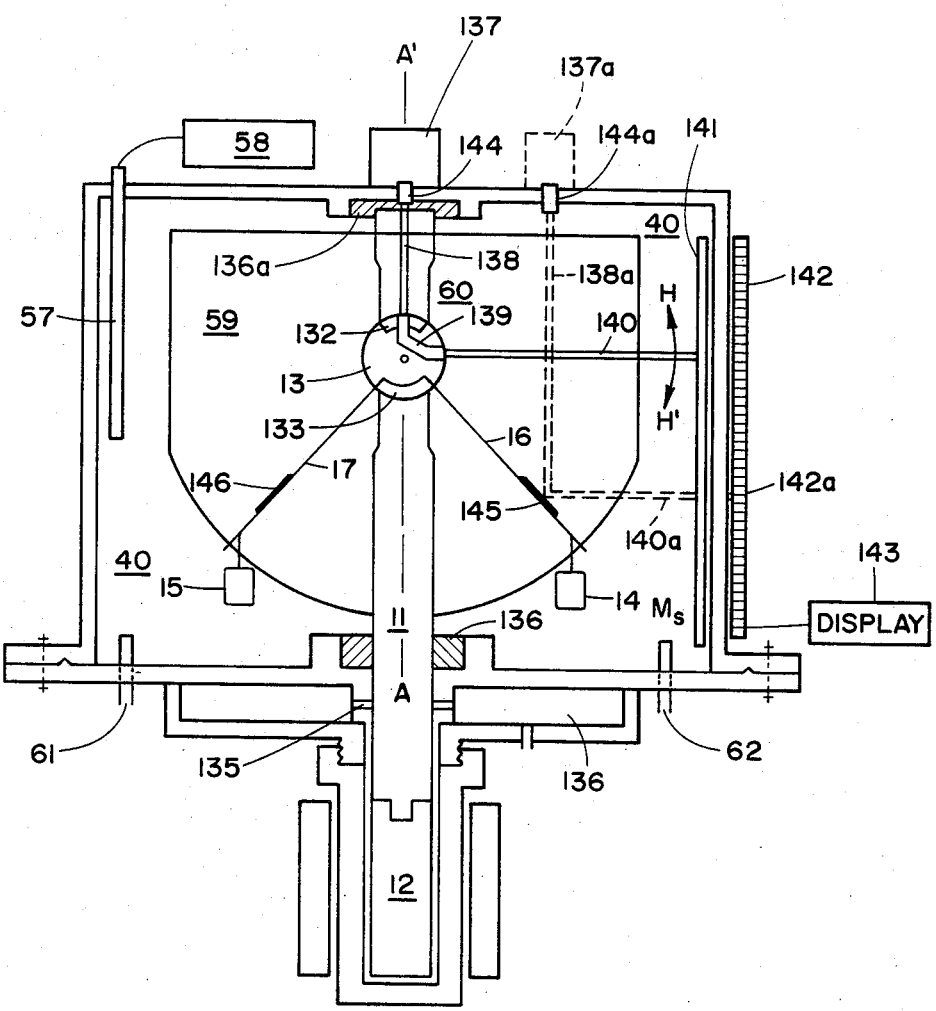
FIG. 13 is an alternate embodiment of the present invention having a plurality of display means for indicating the angular displacement of the rotor in an autoclave.

As illustrated in FIG. 1, the angular displacement apparatus has a first axis of rotation indicated by A-A' which is also the axis of rotation for shaft 11. A means for rotating shaft 11 is illustrated in FIG. 13 as motor means 12. A support means 13 is rotatably mounted on shaft 11 for rotation about a second axis indicated by $r_o$ in FIG. 1. The second axis of rotation is perpendicular to the first axis of rotation A-A'. A test material holding means 14 is illustrated in FIG. 1 in two states; a first static state in which holding means 14 is illustrated in solid lines, and a second dynamic state in which the holding means 14a is illustrated in dotted lines. A reference material holding means 15 is also illustrated in a first static state by solid lines, and in the second dynamic state 15a by dotted lines. A first outwardly extending arm 16 connects the support means or rotor 13 with the test sample holding means and a second outwardly extending arm 17 connects the reference material holding means to the support means or rotor 13. Also mounted on the support means or rotor 13 are a pair of compensator weights 18 and 19, which are once again illustrated in a static state in solid lines, and in a dynamic state in dotted lines as 18a and 19a.

Prior to the operation of the device, the apparatus is balanced by means of adjusting the mass and location of weights 20 and 21 to achieve both static and dynamic balance. A test sample is then placed in the test material holding means 14, and a reference material having a known mass characteristic is placed in the reference material holding means 15.

The apparatus is then rapidly rotated about axis A-A' as illustrated in FIG. 1. Any difference in mass between the test sample and the reference material is reflected by an angular displacement about the second axis of rotation $r_o$. As illustrated in FIG. 1, the test material has gained mass relative to the reference material contained in the container 15. Any change in mass of the tested sample is reflected by a corresponding change in the angular displacement. If for example, the test were one in which the test material were subject to high temperatures to determine what gaseous components might be driven off, the change in mass in the test sample contained in the test material holding means 14 would be reflected by an angular displacement in the opposite direction as the test sample loses mass.

Means for measuring the angular displacement are illustrated in FIG. 1 as a rotating indicator 26 and an angular displacement measurement means 27. Measurement means 27 may be mounted on the shaft 11 by means of vane 30, or may be fixably mounted within an enclosure such as the autoclave illustrated in FIGS. 13-16.

Figures 2A, 2B:
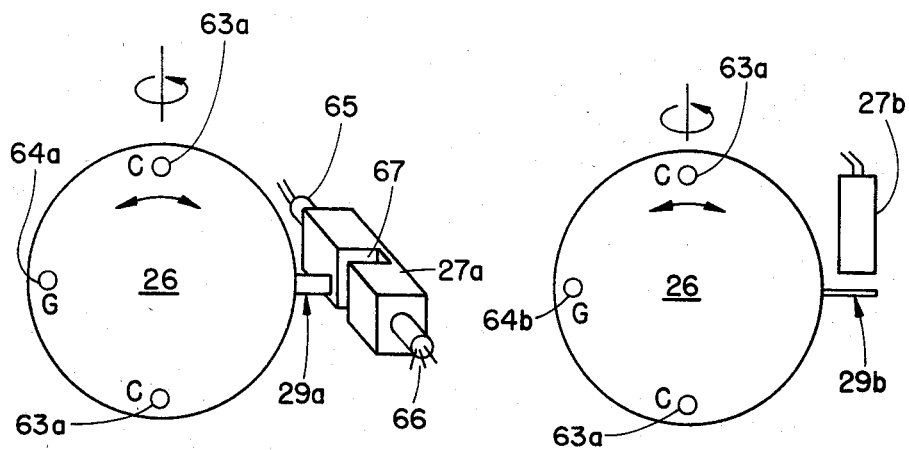
FIG. 2a is a diagrammatic illustration of a light emitter and flag used for measuring the angular displacement of the analyzer.
FIG. 2b is a diagrammatic illustration of a mutual inductance micrometer used to measure the angular displacement of the analyzer.
Figures 2C, 2D:
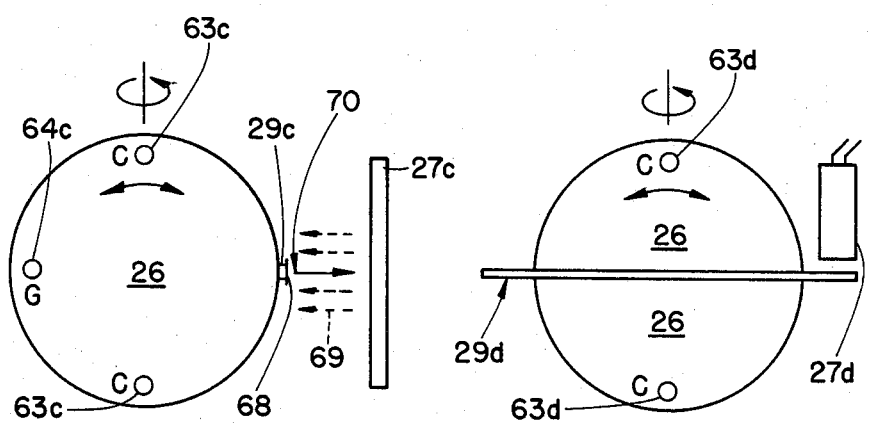
FIG. 2c is a diagrammatic illustration of an optical means including a mirror and a series of micro photo sensors used for measuring the angular displacement of the analyzer.
FIG. 2d is a diagrammatic view of an alternate embodiment using a mutual inductance micrometer mounted on the enclosure for measuring the angular displacement of the analyzer.
Figure 14:
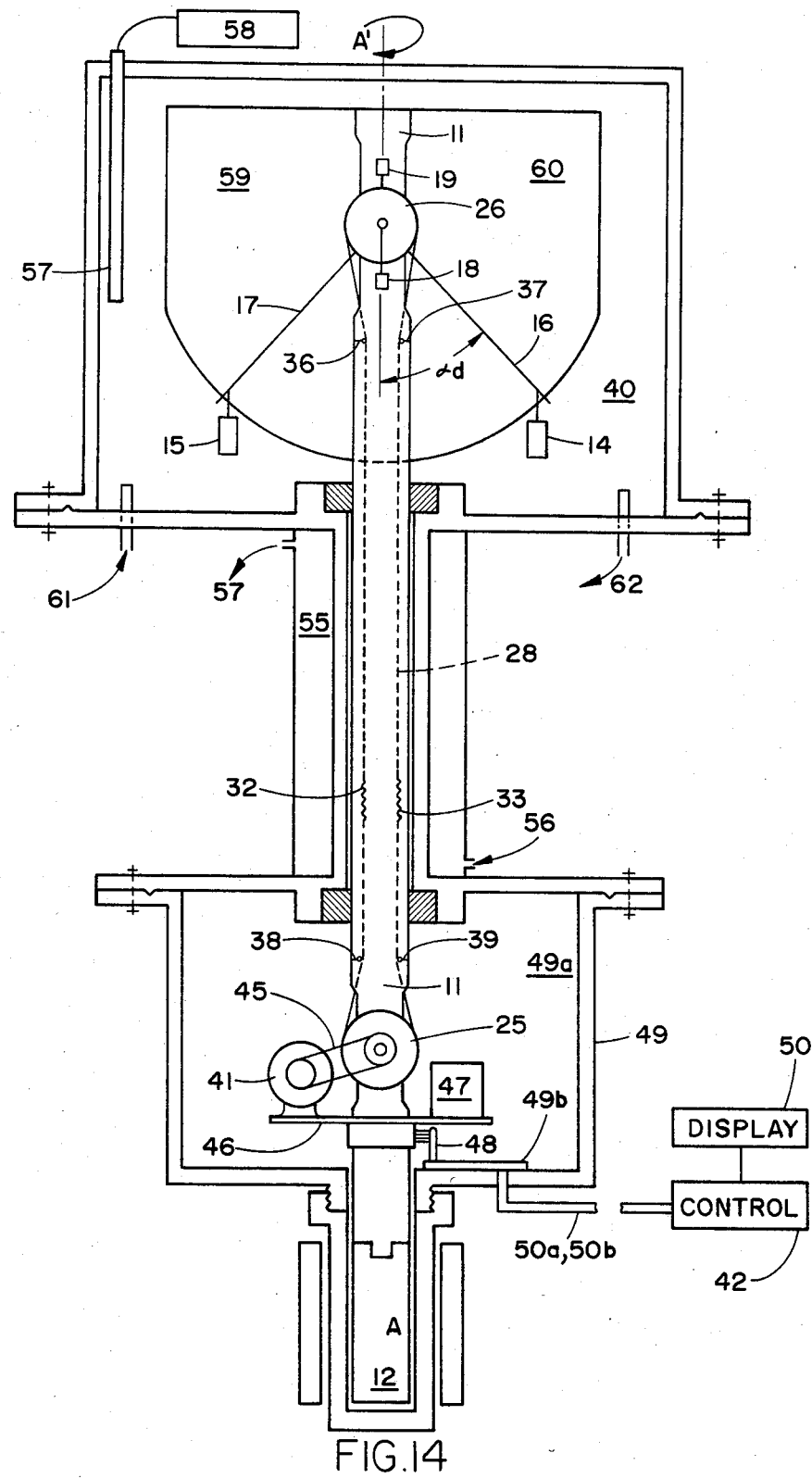
FIG. 14 is a partially cross-sectioned frontal view of a null motor embodiment of the present invention illustrating its use in combination with an autoclave.
Figure 16:
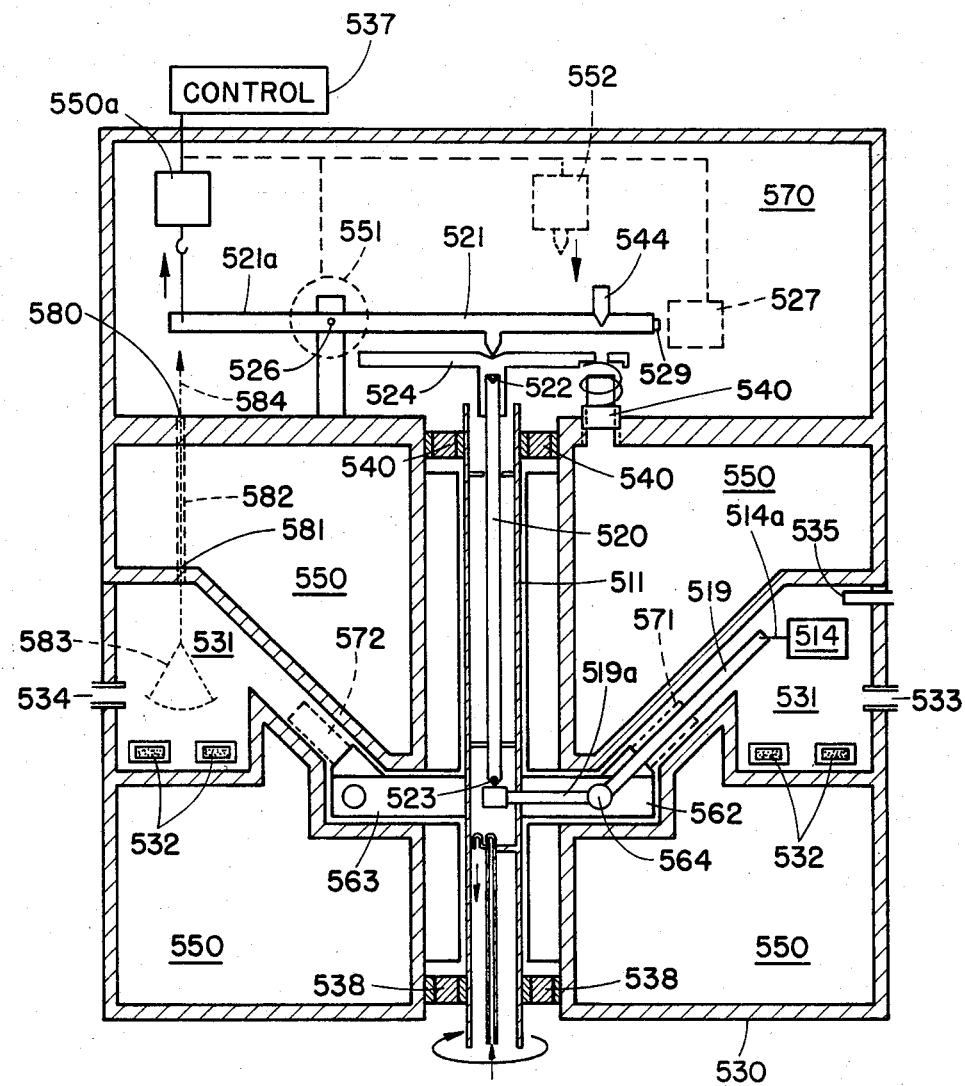
FIG. 16 is a cross-sectional and diagrammatic view of the analyzer illustrated in FIG. 7 as adapted for use in an extremely high temperature autoclave when the device may be used as a thermocentrifugometric mass analyzer, or a conventional thermogravimetric mass analyzer.

A variety of means for measuring the angle of rotation are illustrated in FIGS. 2a-2d to match the instrument to the specific conditions that will be tested or measured. When the instrument is used under extremely high temperature conditions, most electronic transducers would prove to be either inoperable or ineffective because of nonlinear response characteristics. In these cases, optical means such as those illustrated in FIG. 2a and FIG. 2c are considered to be more effective in accurately measuring the angle of rotation. FIGS. 13, 14 and 16 also illustrate other ways of removing the means for measuring the angle of rotation from the autoclave chamber to an external location.

In certain gas-solid and liquid-solid studies, the turbulence of the fluid medium, or the reaction between the fluid and the tested solid may render an optical indication of the angle of rotation extremely difficult to read. In such a case, an electronic transducer such as illustrated in FIG. 2b may be used in lieu of the optical means illustrated in FIGS. 2a and 2c. The various means for indicating the angle of rotation will be herewith discussed in detail with respect to the discussions of the various embodiments of the invention. As illustrated in FIG. 14, a dummy rotor 25 and the rotating indicator means 26 may have different sizes to amplify or reduce the apparent angular rotation about $r_0$. By decreasing the size of the dummy rotor 25 one is able to amplify the apparent angular rotation of rotor 26. This may be desired to improve the accuracy of the angular reading.

Rotor 26 and dummy rotor 25 are connected by means of a flexible drive member 28 which, in a practical application, may be a chain or flexible wire. The material is not important, but it is essential that all materials in the construction of the device illustrated in FIG. 1 be capable of withstanding the temperature and atmospheric conditions to which the test sample will be subjected. When used in the autoclave enclosure illustrated in FIG. 14, the temperatures to which the sample may be subjected may range from 200° to 2500° F.

Figure 10:
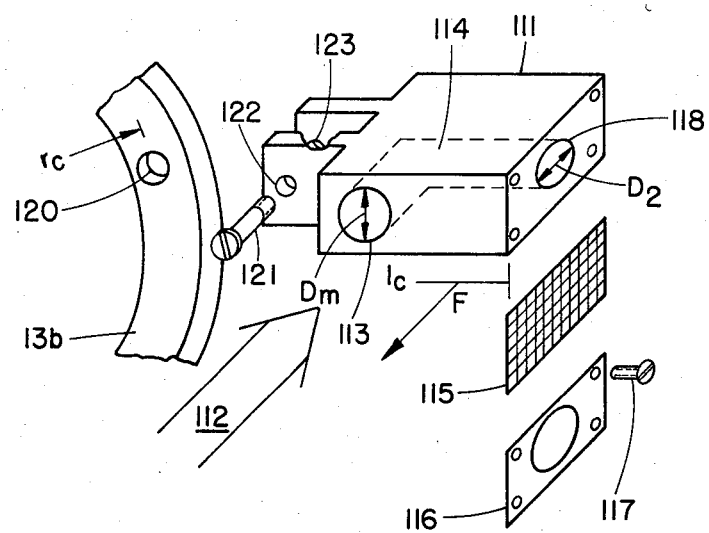
FIG. 10 is an isometric drawing illustrating a second embodiment for the sample retaining means that may be used with any embodiment of the present invention.

The rotor units illustrated in FIG. 1 require a precision design because the instrument is intended to be immersed in reacting fluid and generates the displacement needed for measurement of the mass of the test sample. The rotor disc is thin and light but needs to be relatively strong and rigid and may be constructed of metal, ceramics or quartz. Likewise, the outwardly extending arms 16 and 17 may be formed of metal, ceramic or quartz. The test material holding means 14 and the reference material holding means 15 may be small bowls, or baskets made of light and rigid material. Alternately, the material holding means may be formed with a specific configuration as illustrated in FIG. 10.

With respect to the angular displacement apparatus, the arms 16 and 17 are positioned at 90° from one another to ensure that the net moment of rotation generated by the two rotor arms vanishes in all displacement angles. This positioning also provides the maximum possible angle of displacement in either direction with respect to the net change in mass of the sample being tested. FIG. 1 schematically illustrates in dotted lines the rotational displacement, and Table I (following) mathematically describes the moment of rotation that causes the displacement. The net moment of rotation generated by the two rotor arms vanishes at all displacement angles $\theta$ when the rotor arms are positioned at right angles to each other. A net counterclockwise moment is generated by the baskets and their hangers. This counterclockwise moment is compensated for by a net clockwise moment generated by the compensator weights 18 and 19. A very carefully calculated and designed compensator can reduce the resulting residual moment to a practical moment of zero over the entire range of the operating displacement angle $\theta$. As will be hereinafter described, the desired design angle is $-15°$ to $+15°$. A fine compensation for the net moment generated by the baskets and hangers can be adjusted by adjusting the positions and mass of compensator weights 18 and 19 along their support shafts 18b and 19b so that the residual moment of rotation can be kept at less than: $2.5 \times 10^{-3} \times W^2 M_c r_c \, l_c [1+(l_h/l_c)]$ acting in the direction of $\theta$.

The residual moment vanishes at both $\theta = 0$ and $\theta = \pm 15°$ and is maximum at $\theta = \pm 7.5°$. Other ranges of $\theta$ could be selected, but these could cause imbalance problems (when extremely large) or give insufficient displacement for reading (when extremely small). In addition, the relative angles of rotor arms 16 and 17 could be changed, but 90° has been selected as the optimum operating angle for this embodiment. For other embodiments, a different optimum operating angle may be selected.

When the residual moment of rotation is well compensated, the rotor assembly is dynamically well balanced at all displacement angles, and the ratio of the solid mass $M_s$ the material to be tested (placed in the right hand side container illustrated in FIG. 1) to the reference mass $M_r$ of the reference material (placed in the left hand side container of FIG. 1) is related to $\theta$ by $$\frac{M_s}{M_r} = \frac{[\cos(45 + \theta) + l_c/r_c] \sin(45 + \theta)}{[\cos(45 - \theta) + l_c/r_c] \sin(45 - \theta)}$$

As illustrated in FIG. 1, Table I (following) and the above formula:

$M_s$ is the mass of the sample to be tested
$M_r$ is the mass of the reference material
$M_h$ is the mass of the hanger (14b, 15b)
$M_c$ is the mass of the container (14, 15)
$M_e$ is the mass of the compensator extension arm (18b, 19b)
$M_w$ is the mass of the compensator weights (18, 19)
$l_c$ is the length of the containers and hangers from their point of attachment to the rotor arms 16 and 17
$l_h$ is the length of the hanger arm between the rotor arm and the container
$l_w$ is the length of the compensator weights (18,19)
$r_c$ is the radius of the rotor arms at the point of attachment for the hangers and containers 14, 14b, 15 and 15b
$r_e$ is the radius of the outer ends of the compensator weights 18 and 19
$r_d$ is the radius of the rotor disc 13
W is the speed of rotation of the first axis
T is the moment of rotation about the second axis

TABLE I

| MOMENTS OF ROTATION T/w² |
|---|
| Rotor disc: net:zero |
| Rotor arms: net:zero |
| Container hanger |
| $+M_h r_c^2 [\cos(45 - \theta) + 0.5 (l_h/r_c)] \sin(45 - \theta)$ |
| $-M_h r_c^2 [\cos(45 + \theta) + 0.5 (l_h/r_c)] \sin(45 + \theta)$ |
| net: $-0.707 M_h r_c l_h \sin \theta$ |
| Container |
| $+M_c r_c^2 [\cos(45 - \theta) + 0.5 (l_h/r_c + l_c/r_c)] \sin(45 - \theta)$ |
| $-M_c r_c^2 [\cos(45 + \theta) + 0.5 (l_h/r_c + l_c/r_c)] \sin(45 + \theta)$ |
| net: $-0.707 M_c r_c l_c [1 + (l_h/l_c)] \sin \theta$ |
| Compensator extension arms (two) |
| net: $+2X (0.333) M_e r_e^2 [1 + (r_d/r_e) + (r_d/r_e)^2] \cos \theta \sin \theta$ |
| Compensator weights (two) |
| net: $+2X M_w r_e^2 [1 - (l_w/r_e) + 0.333 (l_w/r_e)^2] \cos \theta \sin \theta$ |
| Solid sample (RHS container) |
| net: $+M_s r_c^2 [\cos(45 - \theta) + (l_c/r_c)] \sin(45 - \theta)$ |
| Reference mass (LHS container) |

TABLE I-continued

| MOMENTS OF ROTATION T/w² |
|---|
| net: $-M_r r_c^2 [\cos(45 + \theta) + (l_c/r_c)] \sin(45 + \theta)$ |

The design and mass of the compensator weights illustrated in FIG. 1 is also based on the values selected for $r_d$, $r_e$, $r_c$, $l_w$, $l_c$, $l_h$, $M_e$, $M_c$ and $M_h$.

In the design of the compensator weights illustrated in FIGS. 1, 2, 11 and 12, the residual moment of rotation is determined by:

$$\frac{T_{residual}}{w^2} = \frac{T_{net, container + hanger}}{w^2} \left[ 1 + \frac{T_{compensator + arm}}{T_{net, container + hanger}} \right]$$

Substituting the values of T listed in Table 1 gives:

$$\frac{T_{residual}}{w^2} = -0.707 M_c r_c l_c [1 + (l_h/l_c) + (M_h/l_h/M_c l_c)]$$

$$\sin \theta \cdot (1 - C \cos \theta)$$

in which compensator constant C is defined as:

$$C = \frac{M_x r_e^2 [[1 - (l_w/r_e) + 0.333(l_w/r_e)^2] + 0.333 M_e r_e^2 [1 + (r_d/r_e) + r_d/r_e)^2]]}{0.354 \cdot M_c r_c l_c [1 + (l_h/l_c) + (M_h l_h/M_c l_c)]}$$

The design of the compensator reduces to selecting a proper value of C so that $\sin \theta (1 - C \cos \theta)$ remains reasonably small over the entire range of the operating displacement angle, $-15° < \theta < 15°$. Two methods are tested in the following. In one, C is selected so that the residual moment vanishes not only at $\theta = 0$ but also at $\theta = 15°$. This is accomplished by chosing $C = 1/\cos 15° = 1.0353$. In the other, C is selected so that the integral of $\sin^2 0(1 - \cos 0)^2$ over $0 < 0 < 15°$ is minimum. This least square fit gives $C = 1.0207$. The values of $\sin 0 (-C \cos 0)$ at various $\theta$ are given below for the compensator constants determined by these two methods.

| 0 | $\sin 0 \cdot (1 - C \cos 0) \times 10^3$ | |
|---|---|---|
| (degree) | C = 1.0353 | C = 1.0207 |
| 0 | 0 | 0 |
| 2.5 | −1.5 | −0.9 |
| 5.0 | −2.7 | −1.5 |
| 7.5 | −3.4 | −1.6 |
| 10.0 | −3.4 | −0.9 |
| 12.5 | −2.3 | 0.8 |
| 15.0 | 0 | 3.6 |

This indicates that the residual moment of rotation is relatively insensitive to the compensator constant over the range $1.021 < C < 1.035$, and either method is acceptable.

Once the compensator constant is selected, one can proceed to design the compensator using the above equation. In the test apparatus, with the following dimensions and mass constants, the above compensator constant equation provided $M_w = 1.16$ g for $C = 1.0353$ and $M_w = 1.17$ g for $C = 1.0207$:

| $r_d$ = 1.3 cm; | $r_e$ = 2.3 cm; | $r_c$ = 8.0 cm |
|---|---|---|
| $l_w$ = 0.75 cm; | $l_c$ = 3.0 cm; | $l_h$ = 1.0 cm |
| $M_e$ = 0.02 g; | $M_c$ = 0.3625 g; | $M_h$ = 0.0120 g |

Thys, a compensator weight of mass 1.16 to 1.17 g appears to be satisfacory for the test apparatus.

In this version of the test instrument, the linearity of the $M_r/M_s$ vs $\theta$ relationship was extremely good over the range of $-0° < \theta < 15°$, and provided the following relationship:

$$M_r/M_s = 1 - 0.0128$$

In this equation, it is understood that $M_s > M_r$ and therefore $\theta$ occurs in the firection of $M_s$. The same equation applies when $M_s < M_r$, but with the left hand side of the equation replaced by $M_s/M_r$. Over the entire range of operable $\theta$, $0° < \theta < 15°$ in either direction, the measurable range of mass ratio is then given by $0.82 < (M_s/M_r) < 1.22$.

The range of mass ratio can then be translated into a window of mass measurement. When the reference mass is chosen to be the average of the initial and final masses of the tested solid, the apparatus is capable of measuring any mass change from a 33% decrease to a 49% increase relative to the initial mass. Larger mass changes can be accommodated by adding inert weights to both containers. For example, a mass change of 1 gram to zero can be measured by adding 2 grams of inert weights so that the total mass decreases from 3 grams to 2 grams, a 33% decrease. The range of mass ratio can be adjusted by varying the length of the container $l_c$ relative to the position of container pin $r_c$. Although $l_c/r_c$ greater than 0.4 is generally less desirable because of the resulting nonlinearity, any $l_c/r_c$ less than 0.4 increases both the linearity and the accuracy by narrowing the range of the mass ratio. Thus $l_c/r_c = 0.2$ gives $0.88 < (M_s/M_r) < 1.14$, or 23% decrease to 30% increase; and $l_c/r_c = 0.1$ gives $0.93 < (M_s/M_r) < 1.08$, or 14% decrease to 16% increase.

The accuracy in the measurement of the mass ratio against the displacement angle is effected by the residual moment of rotation, and its extent is determined by the ratio of the residual moment of rotation to the moment of rotation generated by the reference mass. When the compensator is designed as described above, a maximum of the ratio occurs at $\theta = \pm 7.5°$ and is given by $$\left(\frac{\text{residual moment}}{\text{moment by reference mass}}\right)_{max} = \frac{(2.5 \times 10^{-3}) M_c l_c (1 + l_h/l_c)}{M_r r_c (\cos 37.5 + l_c/r_c) \sin(37.5)}$$

In one embodiment of the invention, a test apparatus was constructed in which
$l_h = 1$ cm
$l_c = 3$ cm
$r_c = 8$ cm
the ratio then became:

$$\left(\frac{\text{residual moment}}{\text{moment by reference mass}}\right)_{max} = 2.0 \times 10^{-3} \cdot M_c/M_r$$

Therefore, insofar as the reference mass exceeded one-fifth of the basket mass, the error caused by the residual moment of rotation could be kept below one percent. As is apparent from the above formula, different proportions of $l_h, l_c, r_c$ and $M_c/M_r$ can also provide improved accuracy.

As illustrated in FIG. 1, in the angular displacement apparatus, the two rotor arms are placed at right angles to each other because the moment of rotation generated by these arms must be exactly compensated for over the entire range of the displacement angles. In the null point apparatus illustrated with respect to FIG. 2, this angle is determined by the total moment of rotation generated by the rotor arms, the mass containers and other parts mounted on the rotor, and need not be 90°. It has been found however that extremely small angles or extremely large angles cause a disturbance in the relative angular displacements of arms 16 and 17. This disturbance can then affect the accuracy of the readings.

As illustrated in FIG. 1, the rotating shaft 11 has attached thereto a pair of vanes 30, 30a, which may be used to agitate the gaseous medium within a autoclave or other enclosure. A transducer means 27 is mounted on vane 30 to respond to flag means 29 which is fixably mounted to indicator disc 26. Transducer means 27 responds to the position of flag 29 to provide an electrical indication of the angular displacement of disc 26 and arms 16, 17. A compensator weight 31 is added to vane 30a to balance the rotational moment generated by the angular displacement measuring device 27. A pair of slip rings 60 and 61 are provided to translate the electrical signals generated by transducer 27 from a rotory environment to a stationary environment. Slip ring 61 is mounted on shaft 11 and rotates with the shaft, while slip ring 60 is stationary, and mounted on a stationary portion of the enclosure. The operation of the transducer means 27 and flag 29 will be hereinafter explained with respect to FIGS. 2a-2d.

FIG. 2a illustrates a physical light obstruction flag 29a and is mounted on rotor 26. The light obstruction flag 29a traverses slot 67 in the transducer 27a as the rotor disc 26 is rotated. A light emitter 65 is used to provide a beam of light that transverses slot 67 and energizes photo-sensor 66. When in the central or nulled position, the light flag 29a totally obscures the light path between the light emitter 65, and the photo-sensor 66. As rotor disc 26 is rotated, however, a gradually larger signal is generated by photo-sensor 66.

Illustrated throughout FIGS. 2a-2d are gravity compensation weights 64a-64c, and centrifugometric compensation weights 63a-63d.

In the embodiment illustrated in FIG. 2b, a metal chip is mounted on the flag 29b. The transducer 27b then takes the form of a mutual inductance micrometer mounted for rotation on vane 30. While it is depicted in a vertical position in FIG. 2b, it should be understood that the positioning of the mutual inductance micrometer 27b could also be as illustrated in FIG. 1, adjacent the flag 29b. The output of the mutual inductance micrometer 27b is then conveyed to the slip ring 61 for output to the stationary slip ring 60 to a display and control means as will be hereinafter later described.

As illustrated in FIG. 2c, a mirror 68 is mounted on the flag 29c. The transducer 27c takes the form of one or more parallel light sources 69 and a series of microphoto-sensors arrayed as illustrated at 27c in FIG. 2c. As disc 26 rotates, the mirror 68 reflects the light back as indicated by arrow 70 to energize one or more of the series of microphoto-sensors. As the rotor 26 is rotated, the relative path light beam 70 traverses the length of the series of microphoto-sensors 27c to provide an indication of the angle of rotation.

As illustrated in FIG. 2d, the flag 29 has been replaced with a circular disc ring, 29d, that serves a similar function to the metal chip mounted on flag 29b illustrated in FIG. 2b. The transducer 27d is again a mutual inductance micrometer that may be fixably mounted in the enclosure. Inasmuch as the flag 29d is a continuous circular ring, it will provide a steady output signal for the mutual inductance micrometer that is a function of the angular rotation of disc 26. As illustrated in FIG. 2b, the transducer 27b, is mounted on the rotating portion of the apparatus will provide a steady output that is function of the distance between the metal chip and the inductance micrometer. If the transducer 27b illustrated in FIG. 2b is mounted on the enclosure, then the metal chip 27b would generate a series of pulses, the amplitude of which would vary as the disc 26 is rotated. By utilizing the angular ring illustrated in FIG. 2d, a steady output signal is derived which is a function of the angular rotation of disc 26.

DETAILED DESCRIPTION OF THE NULL MOTOR APPARATUS

Figure 3:
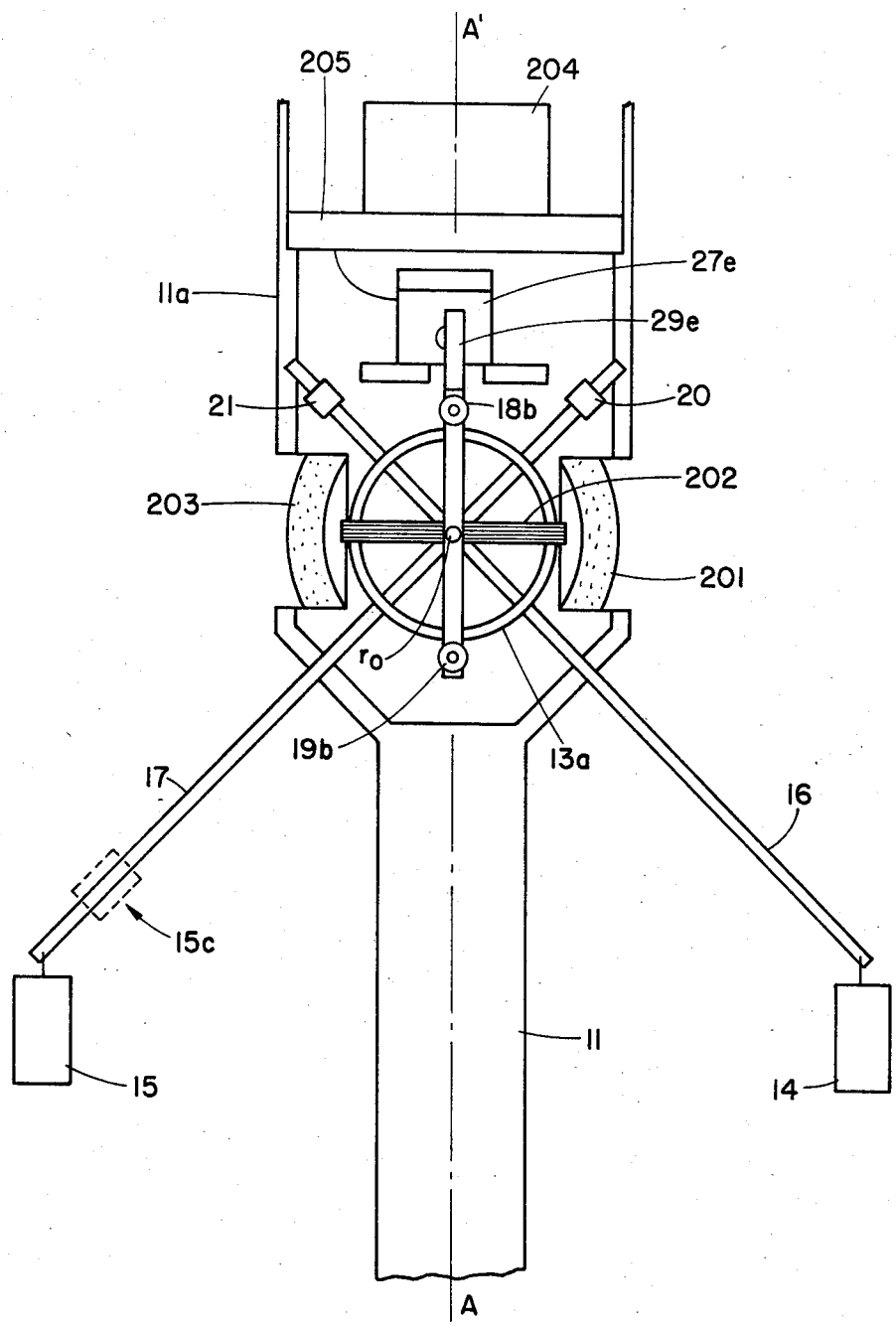
FIG. 3 is a partially cross-sectioned frontal view of a null motor embodiment of the present invention.

FIG. 3 illustrates a second embodiment of the thermocentrifugometric analyzer wherein the angular displacement of the rotor 13a is opposed by a null motor apparatus which senses the angular displacement of the rotor and generates a counter reactive force to restore to its original position. The amount of reactive force necessary to maintain the rotor at the null point is then used to measure the mass of the sample. While the device illustrated in FIG. 3 is illustrated in a static position, it is understood that it rotates rapidly on shaft 11 about axis A-A' as was previously explained with respect to FIG. 1. Rotor arms 16 and 17 suspend a sample holder 14 and a reference weight holder 15. Alternately, a reference weight basket 15 may be replaced by a fixed and linearly displaceable weight 15c illustrated in dotted lines in the lower most portion of arm 17 in FIG. 3. The mass of weight 15c is used to compensate for the mass of basket 14 and the initial loading of the sample material in basket 14.

A coil 202 is formed about rotor 16a as will be hereinafter explained with greater detail with respect to FIG. 4. A current is supplied to coil 202 through stationary slip ring commutator 204 and rotory slip ring commutator 205 illustrated in the upper portion of the device in FIG. 3. The commutators 204, 205 have been illustrated in schematic form inasmuch as a variety of commutator configurations could be used to transmit the current from the stationary housing to the rotating rotor.

A fixed magnet 201 is supplied on one side of rotor coil 202, and a variable electromagnetic coil 203 is placed on the other side of rotor coil 202. The current for coil 203 is also supplied through the stationary commutator 204 to the rotating commutator 205 in a manner similar to that supplied to coil member 202. In addition, if the loading of the device warrants, the magnetic field crossing the coil may be enforced by placing a highly permeable ferromagnetic material inside, but not in contact with the rotor 13a. In addition, a polarized electromagnet may be used to strengthen the magnetic field surrounding the coil 202.

Application of a current to coil 202 will result in magnetic lines of force aligned along axis A-A'. The use of magnets 201 and magnets 203 will tend to maintain the coil 202, and thereby rotor 13a in the position illustrated in FIG. 3. As a change in mass is experienced in container 14, the imbalance will generate a rotational moment about $r_o$ at the center of rotor 16a. If there is a change in mass wherein the sample in container 14 loses mass, rotor arm 16 will be displaced downwardly as illustrated in FIG. 3. If the reaction generates additional mass in the sample contained in basket 14, rotor arm 16 will be displaced upwardly. The relative rotational moment of rotor arms 16 and 17 about $r_o$ is opposed by the electromagnetic force generated on coil 202 subjected to the magnetic field generated by magnet 201 and coil 203. The relative rotational displacement of rotor 16a is measured by flag 29e, and transducer 27e in a manner similar to that previously described and illustrated with respect to FIGS. 2a-2d. Either a light detector, or a mutual inductance micrometer may be used. Any change in the position flag 29e will immediately be detected by transducer 27e, and communicated via slip ring commutators 204 and 205 to the electronic control circuitry for the thermocentrifugometric mass analyzer. Appropriate corrective currents will then be supplied through the stationary slip ring commutator 204, and the rotory commutator 205 to coil means 203 to apply a corrective force to armature coil 202 that surrounds rotor 13a. By measuring the change in current supply to coil 203 that is required to rebalance rotor 13a to its central nulled position, one is able to determine a functional value that is representative of the change of mass in the sample contained in basket 14.

The details of the device illustrated in FIG. 3 are further illustrated in FIGS. 4–6. The rotor 13a comprises an elongate cylinder having a coil 202 wrapped around its center axis. Rotor 13a is supported for rotation by means of pins 208 and 209 in jeweled bearings 210 and 211. The jeweled bearings 210 and 211 are secured by jewel ring holders 212 and 213 which are threadably secured in apertures 214 and 215 (not shown) in shaft 11a as illustrated in FIG. 5. The use of pins 208, 209, and jeweled bearings 210 and 211, together with the threadable jewel ring holders 212 and 213 provide for very precise positioning of the rotor 13 within the enlarged shaft member 11a. The compensator weights 206 and 207 are secured to rotor 27a by means of rods 216 and 217. While end brackets 206 and 207 form part of the compensator weight, additional compensator weights may be provided as illustrated at 218–221 to compensate for the coil balance displacement flag or other structural features of the rotating parts of rotor 13a. The flag means 29e reciprocates within slot 67e as rotor 13a pivots about pins 208 and 209. In doing so, it varies the output of photo-sensor 66e. A light emitting diode, or other light emitter 65e is focused on photo-sensor 66e, and is occluded when in the central balanced or nulled position by means of flag 29e.

As illustrated in FIG. 5, shaft 11 contains an enlarged portion 11a for containing the rotor 13a. Formed within the enlarged shaft portion 11a is a transducer mounting plate 222 having a slot 223 formed therein for receiving the flag 29e. In addition, when used in an extremely high temperature environment, the rotor is equipped with high temperature shielding or radiation reflecting means 224 which is more fully illustrated in FIG. 6. The conical portion 11b of shaft 11 is protected by means of insulation 224a and a radiation reflector 224b to prevent the intense heat generated by the high temperature autoclave from reaching the electrical components mounted within the enlarged shaft 11a. The need for the radiation reflector and insulation will be more fully illustrated with respect to the device illustrated in FIG. 15.

An alternate embodiment for the null point apparatus for measuring the change in mass in accordance with the principles of the present invention is illustrated in FIG. 14. As illustrated in FIG. 14, a rotary disc 13, the support arms 16 and 17 and the baskets 14 and 15 are essentially the same as those described previously with respect to FIG. 1. Although it is illustrated in a static position in FIG. 2, in operation it is rapidly rotated about axis A-A' by means of shaft 11 and motor means 12. The relative angular displacement of rotor 13 is transferred by the flexible linkage 28 to dummy rotor 25 which is now mounted below the autoclave chamber 40. The flexible drive means 28 is guided by means of rollers 36, 37, 38 and 39 within shaft 11 to provide a relatively friction free transfer of the relative angle of rotation from rotor disc 13 to dummy disc 25. Tensioning means 32 and 33 maintain appropriate tension level on flexible drive means 28. In the preferred embodiment, a thin wire chain was used to transfer the angular rotation from rotor 13 to dummy disc 25. As indicated previously with respect to FIG. 1, the angular displacement can be read directly by optical means, or can be converted into an electrical signal by hydraulic, electrical, magnetic, or optical means. In the null point apparatus illustrated in FIG. 3 however, the angular displacement generates an electrical signal in a displacement measuring means 43 (illustrated in FIG. 11). Control means 42 is responsive to the signal and responds by energizing motor means 41 to generate a reactive force along drive means 45 to the dummy rotor 25. The reactive force is then transmitted by a flexible drive means 28 to the rotor 13. In the null point apparatus, motor 41 is a two poled DC motor placed on a supporting frame 46 which is fixed on rotating shaft 11. A compensator weight 47 is provided to maintain an effective balance for the null point apparatus during the high speed rotation of shaft 11. A pickup brush 48 is used to transfer the input and output signals and power for motor means 41 from the stationary support 49b to the rotating shaft 11. The electrical signals picked up by brush 48 are transmitted by a control line 50b to the control unit 42.

Figure 11:
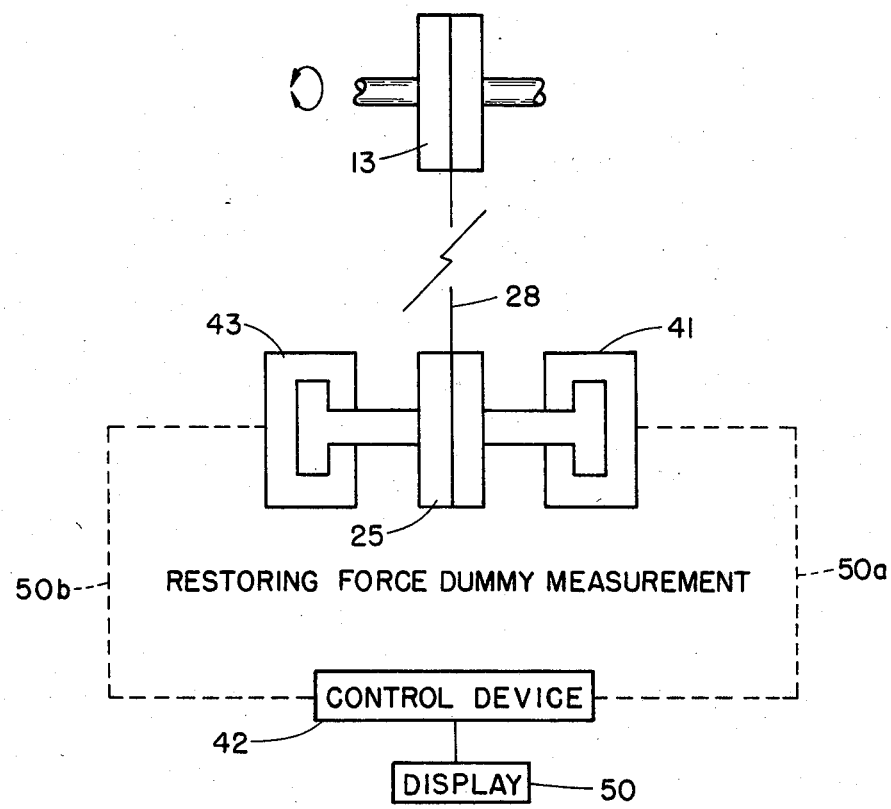
FIG. 11 is a schematic illustration of a null motor embodiment of the analyzer illustrated in FIG. 14.

A schematic of the null point apparatus is illustrated in FIG. 11 wherein 13 refers to the rotor, 25 the dummy rotor, 41 the motor means, and 43 the displacement measuring means for measuring the angular displacement of dummy disc 25. The signal generated by measuring means 43 is transmitted by control line 50b to control device 42 which energizes the motor 41 through control line 50a to restore the angular rotation of dummy disc 25 to its central "nulled" position. The restoring force is then transmitted along the flexible means 28 to rotor 13.

As illustrated in FIG. 14, the invention is particularly adapted for use in a heated autoclave unit for high temperature reaction studies. The instrumentation chamber 49a can be protected from being overheated by providing a cooling jacket 55 having a source of cooling water at 56 and an outlet for the coolant at 57. This not only provides for cooling of shaft 11, but also insulates the autoclave unit 40 from the instrumentation chamber 49a. The autoclave unit 40 utilizes conventional means for heating the interior of the chamber to extremely high temperatures. These studies may be conducted at any temperature from 200° to 2500° F. An instrumentation probe 57 is connected to a control means 58 for maintaining the autoclave at the desired thermal temperature(s). In addition to the thermocentrifugometric analyzer, the rotating shaft 11 also has a pair of agitator blades 59 and 60 to enhance gas mixing within the autoclave. In addition, electrical heating elements may be placed in the agitator blades 59 and 60 to assist in maintaining the interior of the autoclave at a constant temperature. A gas inlet conduit 61 and a gas outlet conduit 62 are provided for admitting and discharging reactive gases when it is desired to conduct a mass analysis with a specific gas in lieu of ambient atmospheric air. If desired, the gas inlet may be placed directly in line with the dynamic position of containers 14 and 15 to direct high speed impingement of the gas supplied through conduit 61 into the path of container 14. In addition, chamber 40 may be pressurized by means of conduit 61 and 62 to provide mass analysis under high pressure gas conditions.

The control device 42 is equipped with a suitable display 50 for indicating the amount of the reactive force generated by motor means 41 and applied to the rotor disc 13. Alternately, it may display a derivative signal which is indicative of the change in mass indicated by the amount of reactive force needed to maintain dummy disc 25 and rotor 13 and their central "nulled" position.

DETAILED DESCRIPTION OF BALANCE BEAM APPARATUS

In the third embodiment of the present invention, one or more rotor arms are provided which are pivotally biased against a balance beam by means of a reciprocating piston connected between the beam and the rotor arm. Means are provided for calibrating the balance beam to provide a known reactive force for the sample as it is subjected to centrifugal force. After a first reference force is generated by the balance beam, to affect the apparent mass of the sample, any change in mass in a test sample will be measured directly by a change in the balance beam position.

The reciprocating piston displacement apparatus may be distinguished from the above devices inasmuch as a single angularly displaceable arm 319 is provided for rotation about a first axis A-A' as was previously described with respect to FIGS. 1 and 3. A known and adjustable reference force is provided on the reciprocating shaft 320 that is aligned along the first rotational axis A-A', and the angular displacement of the rotating arm and tested solid exert a compressive or extensive force on the piston. A balance beam measurement means 321 is used to measure the vertical displacement of the piston caused by the difference between the reference force and the force generated by the rotating arm and the tested solid. The displacement is then used to determine the mass of the tested solid by means of a calibration formula established prior to the operation through a series of mass measurements on various reference weights of known mass. A derivative value of the displacement is used to determine the corresponding derivative value of the change in mass as the tested solid is subjected to preselected temperature and fluid conditions.

Figure 7:
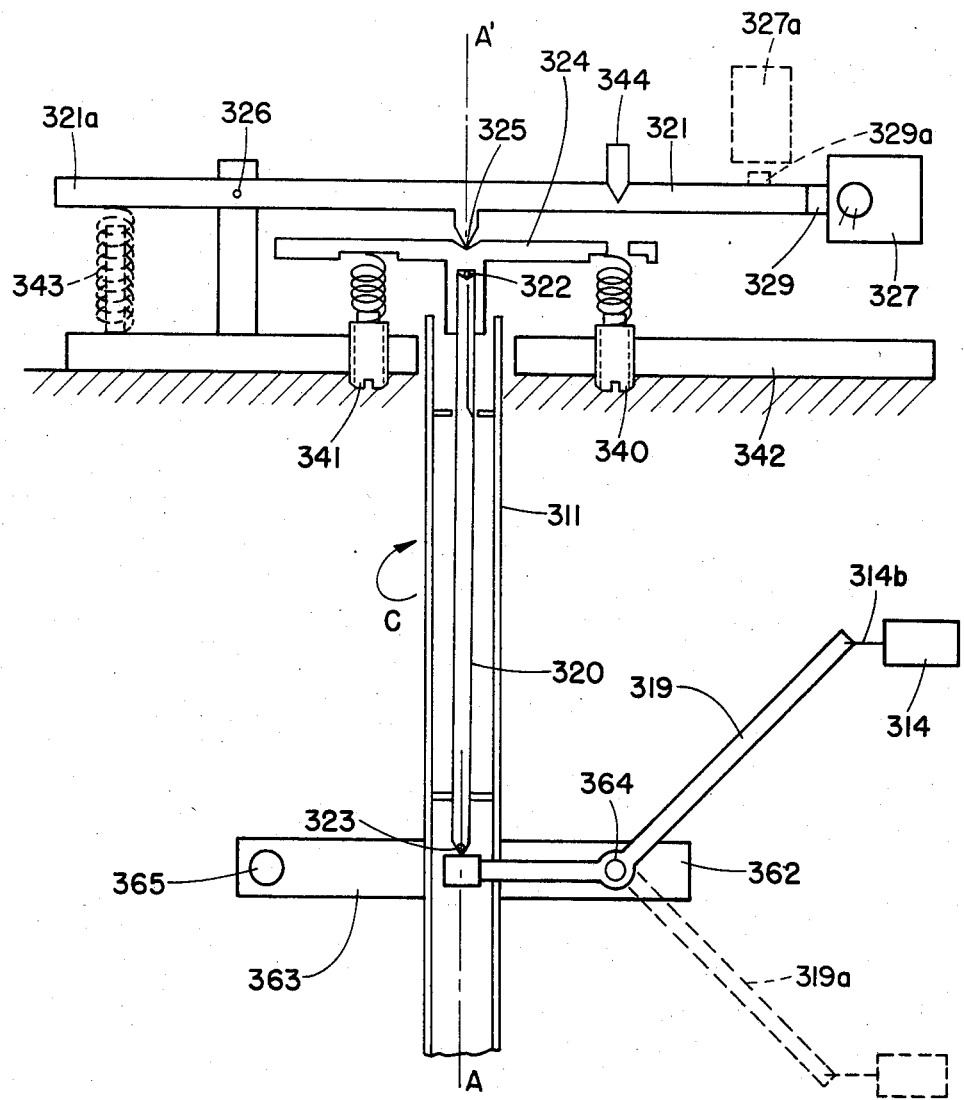
FIG. 7 is a cross-sectional and diagrammatic view of another embodiment of the invention utilizing a reciprocal rod and balance beam.

As indicated in FIG. 7, the displaceable arm 319, may be angled upwardly as illustrated by the solid lines, or angled downwardly by the dotted lines 319a. The material to be tested is placed in basket 314 which is suspended from arm 319 by means of hanger 314b. The rotational movement of shaft 311 is imparted to the reference container by means a motor as illustrated in FIGS. 13 and 14. Support arms 362 and 363 may also serve as circulatory vanes to agitate the fluid or gaseous mediums surrounding the sample container 314. The compensator weight 365 is provided on arm 363 to compensate for the relative mass of arm 319 and 319a, and the weight of basket 314. As the device illustrated in FIG. 7 is rotated about axis A-A', a rotational moment is generated about axis 364 urging the rotor arm 319 outwardly and displacing the reciprocating shaft 320 upwardly as illustrated in FIG. 7. Reciprocating shaft 320 is provided with bearing means 322 and 323 which are used on either end of reciprocating rod 320 to minimize the frictional drag that may be generated between the rotation of rotor arm 319a caused by the rotating of shaft 311, and the stationary position of balance beam 321. To further assist in translating the rotary forces to a stationary balance beam, an adjustable platter 324 is provided between the reciprocating shaft 320, and the balance beam 321. A jeweled bearing 325 is used between the platter and the balance beam to translate the vertical movement of reciprocating rod 320, to the angular movement of balance beam 321, about axis 326. The relative movement of balance beam 321 may be detected by transducer 327 or 327a (illustrated in dotted lines) in a manner previously illustrated with respect to FIGS. 2a–2d. As illustrated at 327, a photo-optical transducer is used with a flag 329 attached to the end of balance beam 321. Alternately, a metal chip or magnet 329a may be attached to the balance beam to activate a micro inductive coupler 327a.

A plurality of spring loaded adjusting screws illustrated at 340 and 341 in FIG. 7 are used to precisely align platter 324 in a horizontal position with respect to stationary support means 342.

In operation of the device illustrated in FIG. 7, the mass $M_s$ of the test sample is compensated for by means of an adjustable spring means 343 which exerts a compressive or upward force on balance beam 321a. An adjustable weight 344 is moved along balance beam 321 to a predetermined position that is determined by the weight of the sample to be placed in test sample basket 314. A predetermined position of light 344 is calculated for a variety of rotational speeds for shaft 311 and a variety of weights in said $M_s$ that may be placed in basket 314. Thus, in the operation of the device, when the shaft 311 has reached its predetermined rotational speed, with mass $M_s$ in basket 314, the balance beam will be balanced. The force generated by spring balance 343, and the position of displaceable balance weight 344 is balanced against the apparent mass of the rotation sample at a predetermined speed. As the sample $M_s$ gains or loses mass in its reaction with the fluid or gaseous medium surrounding basket 314, the rotational force is first generated about axis 364, which is translated into vertical reciprocation of reciprocating shaft 320. The vertical movement is then translated through platter 324 to balance beam 321, and measured by transducers 327 or 327a.

Figure 8:
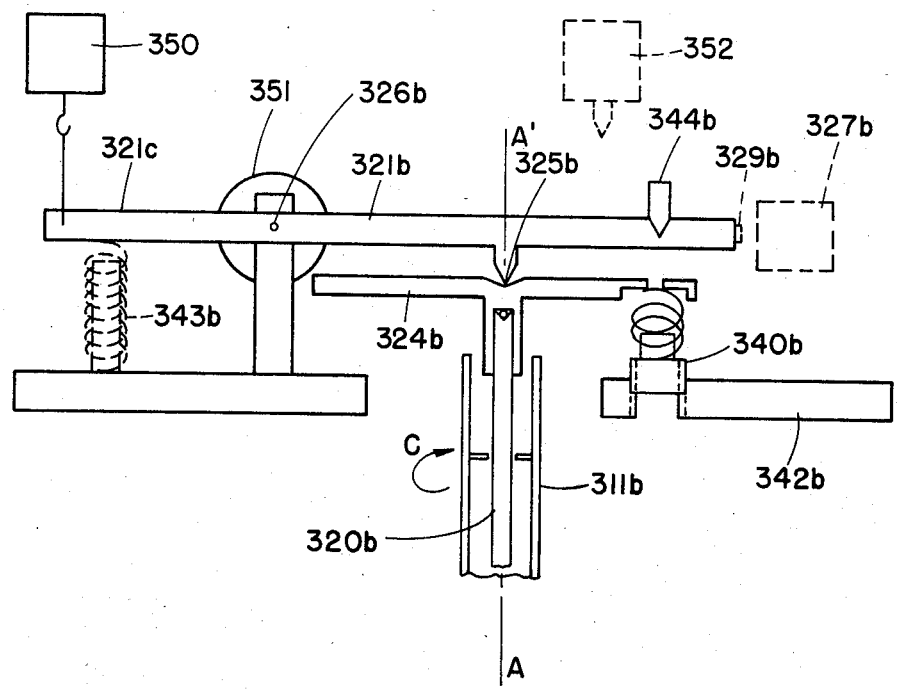
FIG. 8 is a diagrammatic view of several alternate means that may be used to generate compensating forces to "null" the balance beam illustrated in FIG. 7.

The embodiment illustrated in FIG. 8 generates reciprocal forces along reciprocating shaft 320b in a manner identical to that previously described with respect to FIG. 7. The forces generated along balance beam 321b, however, are different from those generated along balance beam 321 and 321a illustrated in FIG. 7. A variety of means illustrated as 350, 351 and 352 may be used to provide a compensating or restoring force to the balance beam to maintain it in a central or nulled position. The amount of force necessary to restore the balance beam to its' nulled position may also be derived by means of more than one technique.

As was previously illustrated with respect to FIG. 7, the upwardly generated force at point 325b on balance beam 321b is opposed by spring means 343b, insofar as the force is generated by the mass of arm 319 and hanger 314. The force generated by $M_s$ at the rotational speed and weight selected and placed in hanger basket 314 is compensated for by adjustable weight 344b. Means 350, 351 and 352 all provide means of generating additional compensatory forces to restore the balance beam to a central nulled position. In a first version of the null device, the transducer 327b detects movement of a metal or magnetic chip 329b on the balance beam 321b. As movement of the balance beam is detected, a compensating force is applied by any one of the means 350, 351, or 352. The device illustrated at 350, is an adjustable point gravimetric balance which will apply a counter force to spring 343b, depending upon the electrical force transmitted to it by appropriate control circuitry (illustrated in FIGS. 11 and 14). Alternately, a motor 351 may be used to exert a rotational torque about axis 326b on balance beam 321b. In a third embodiment of the null point balance beam apparatus, a compressive type null device 352 may be used in lieu of the adjustable weight 344b to provide an adjustable downwardly displaceable weight on balance beam 321b. As the balance beam 321b is deflected upwardly or downwardly by a change of mass $M_s$ in container 314, the amount of force generated by the compressive type null device 352 changes to restore the balance beam 321b to a center nulled position.

Alternately, the device 351 illustrated as a motor in FIG. 8, may be replaced by a displacement measuring means to measure the angular displacement of balance beam 321b. The control device (not shown) will then cause a compensating force to be generated by means 350 or 352.

While an electrical means has been disclosed in FIGS. 11 and 14, it should be understood that the compensating forces generated by means 350, 351 and 352 could be created electrically, hydraulically, magnetically, or neumatically, as desired. Each of the respective modes of operation has distinct advantages, depending upon the operating parameters and conditions in which the device will be operated.

Figure 17:
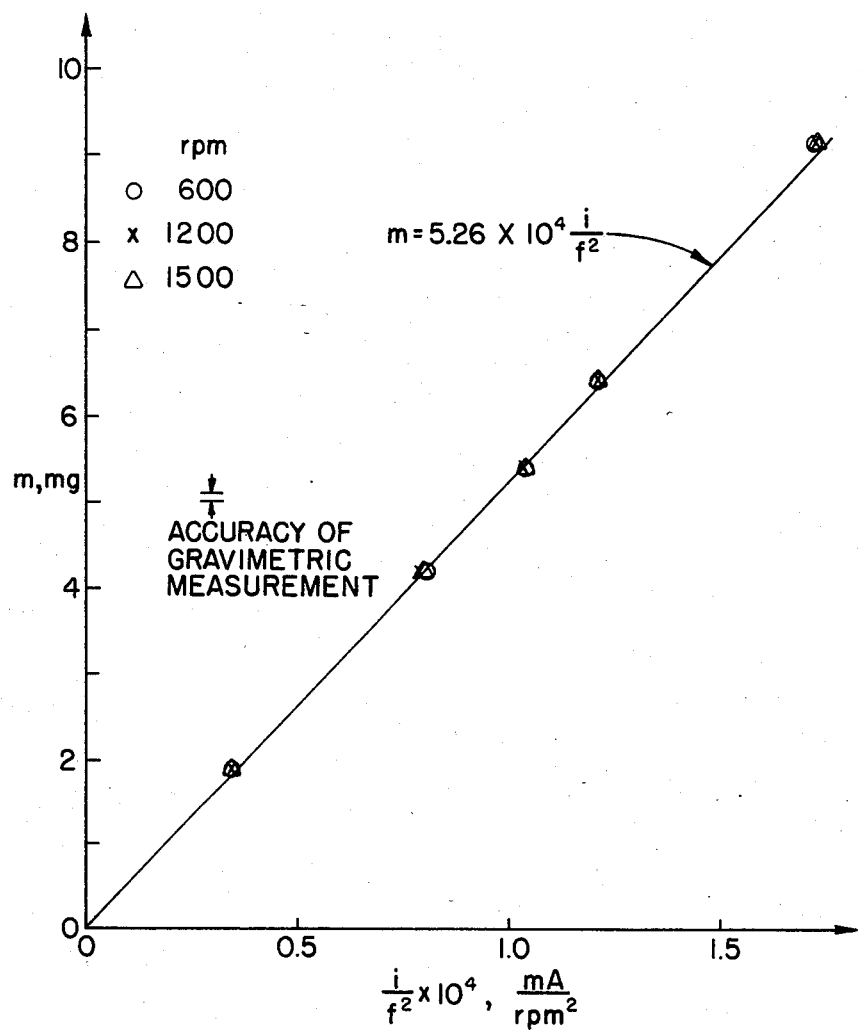
FIG. 17 is a graph illustrating the accuracy of a null motor thermocentrifugometric mass analyzed for the $M_s$ values and rotational speeds listed in Table 2.

The test results from a thermocentrifugometric mass analyzer using a null motor to generate a counter restoring force is illustrated in FIG. 17, using the $M_s$ values and rotational speed listed in Table 2.

TABLE 2

| Test solid mass* $M_s$ (milligrams) | Null current required (milliamperes) | | |
|---|---|---|---|
| | 600 rpm | 1200 rpm | 1500 rpm |
| 1.9 ± 0.1 | 12.5 | 50.0 | 79.0 |
| 4.2 ± 0.1 | 29.0 | 115 | 180 |
| 5.4 ± 0.1 | 37.5 | 150 | 235 |
| 6.4 ± 0.1 | 43.5 | 175 | 275 |
| 0.2 ± 0.1 | 62.5 | 250 | 390 |

*measured by a conventional gravimetric balance with an accuracy of 0.1 milligrams.

As illustrated in FIG. 17, using the null motor balance, the null current required, i, is proportional to the test solid mass, $M_s$ and the square of the rotational speed, f, or $$i = \frac{1}{K} M_s f^2 \text{ or } M_s = K \frac{i}{f^2}$$

in which the proportionality constant, K can be calculated from the geometry of the coil and the magnetic field strength. However, when the magnetic field strength is difficult to measure, a plausible alternative to the calculation procedure is to determine it from a linear regression of preselected test data. Thus for this particular balance $$K = 5.26 \times 10^4$$

when i is in milliamperes, $M_s$ is in milligrams and f is in rpm. As illustrated in FIG. 17 the gravimetrically measured $M_s$ is plotted against $i/f^2$.

As can be seen in FIG. 17, the accuracy of a test prototype null-motor balance exceeds 0.1 milligrams. Further mechanical improvement of the test device should result in a thermo centrifugometric mass analysis having an accuracy in the nanogram range.

DESCRIPTION OF THE ALTERNATE VARIATIONS

FIGS. 9-16 illustrate additional embodiments and variations that may be applied to any one or more of the four mechanical devices illustrated in FIGS. 1, 3, 7 and 8.

Figure 9:
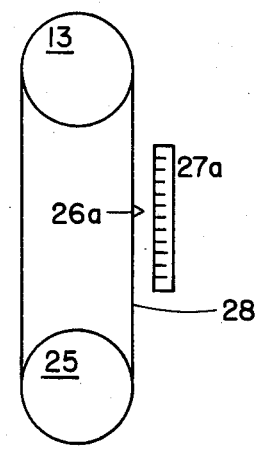
FIG. 9 is diagrammatic illustration of a mechanical means used for providing a readout indicative of the angular displacement of the present analyzer.

FIG. 9 illustrates an alternate display means that may be used when it is necessary to separate the rotor 13 and a dummy display disc 25. The relative rotation of disc 13 and a dummy disc 25 is measured along the transfer device 28 by positioning an indicator means 26a to reciprocate along a displacement measuring means 27a which may be positioned on or outside the rotating shaft 11. A variety of stroboscopic, optical, electrical and other techniques may be used to measure the linear reciprocation of indicator 26a.

Figures 12, 12A:
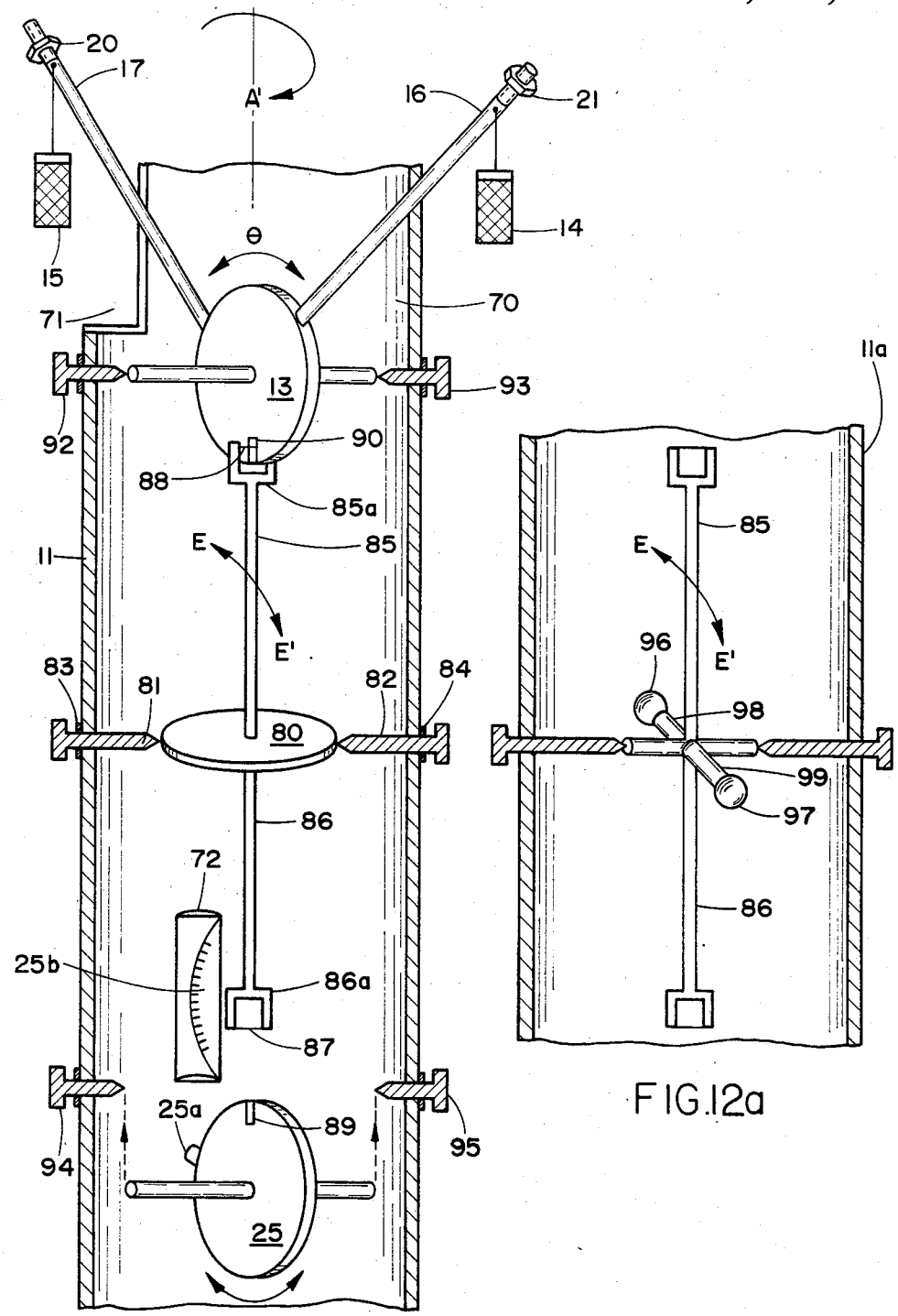
FIG. 12 is a partially cross-sectioned and diagrammatic view of a transfer means for translating the angular motion of a first rotor to a second rotor that provides an indicator means for the angular displacement for the first rotor.
FIG. 12a is an alternate configuration of the transfer means illustrated in FIG. 12.

As illustrated in FIG. 12, a transfer linkage is provided for transmitting the rotation of rotor 13 to a dummy rotor 25. In the embodiment illustrated in FIG. 12, the rotor 13 is positioned within shaft 11, with the outwardly projecting arms 16 and 17 extending through slits or openings 70, 71 in the walls of shaft 11. Likewise, a third opening 72 provides means for the indicator 25a to display a degree of angular rotation along scale 25b when the rotor 13 is displaced along angle $\theta$.

The transfer arrangement described in FIG. 12 may be termed a gyroscopic lever transfer element. A gyroscopic disc 80 is positioned within the rotating axis A-A' of shaft 11 by virtue of threaded pins 81 and 82. Lock nuts 83 and 84 are provided to maintain an exact placement of the point support mechanism provided by pins 81 and 82. The size and mass of the gyroscopic disc 80 is determined against that of the gyroscopic axis E-E' so that no net rotational force is exerted in either direction at all angular displacements from the vertical null position. This precise balancing is possible because the axis A-A' is perpendicular to disc 80. The transfer linkage comprises arms 85 and 86 each of which have bifurcated ends 85a and 86a with wire blades 87 and 88 spanning the bifurcation. The wire blades 87 and 88 fit within slots 89 and 90 of dummy disc 25 and rotor 13. This engagement enables a smooth and frictionless transfer of the angular displacement from rotor disc 13 to dummy disc 25. The rotor 13 is likewise held in the center axis A-A' of rotating shaft 11 by virtue of holding pins 92 and 93 while the dummy disc is secured by pins 94 and 95. Each of these pins is also equipped with a locknut or other similar device to securely position the rotating elements within the shaft without exerting and undue frictional forces thereupon. As illustrated in FIG. 12a, the gyroscopic disc 80 may be replaced by a pair of compensator weights 96 and 97 which are suspended from arms 98 and 99.

The transfer linkage illustrated in FIGS. 12 and 12a has three distinct advantages over the transfer chain illustrated in FIGS. 9 and 14. First, each unit of the thermocentrifugometric analyzer consisting of the rotor disc unit 13, the transfer unit 80, and the instrumentation disc 25, can be precisely balanced before assembling. Secondly, the gyroscopic lever transfer mechanism illustrated in FIG. 12 is free from thermal expansion problems which may arise with the transfer chain 28 at extremely high temperatures. While the centrifugal force of the device and the spring means illustrated in FIG. 14 will also compensate for thermal expansion of the flexible transfer means 28, the gyroscopic lever transfer device is simpler and requires no such compensation. Finally, the gyroscopic lever transfer device makes it possible to measure the angular displacement in the transfer unit rather than in a gas chamber or in the instrumentation chamber. By measuring the angular displacement along E-E', the relative rotation of the transfer mechanism can be easily measured.

Each of the principal embodiments previously illustrated with respect to FIG. 1, 3, 7 and 8 disclose an angularly extending arm having a basket suspended therefrom for receiving a test sample to be measured. FIG. 10 describes an alternate embodiment of the sample holding means wherein the rotor 13 is replaced with a rotor ring 13b and a unique solids container 111.

The test samples to be measured may come in a variety of sizes ranging from large particles to very fine powders. For big particles, a loosely woven basket such as that illustrated in FIGS. 1,3 is quite satisfactory since the weave, in comparison to the size of the tested particles, allows the fluid or gas to pass freely between the solids. The basket configuration however is not satisfactory for very fine powders because even a small layer of such powders would force the fluid to deflect and pass around the container. In the example illustrated in FIG. 10, the fluid path 112 to be impinged upon the test sample to be analyzed is directed at the solids container 111 to enter the mouth 113 of the container. The solids container 111 has drilled therein a duct 114 illustrated by the dotted lines in FIG. 10. The duct terminates in a discharge screen 115 which is secured to the solids container 111 by welding or by means of plate 116 and a plurality of screws, one of which is illustrated on 117. The fluid flow through the duct 114 can be further increased by placing an air foil at the discharge end, or by making the diameter of the mouth 113 ($D_m$) somewhat larger than the diameter of the discharge exit 118 ($D_2$).

As illustrated in FIG. 10, $r_c$ is the distance from $r_0$ to the pivot point on support means 13b. $l_c$ is the distance from the particulate screen 115 to $r_c$. As illustrated in FIG. 10, the transition between $l_c$ and $r_c$ is at the center axis of opening 120 which receives the pivot pin 121 as it passes through openings 122, 120 and 123. Pivot pin 121 thereby allows solids container 111 to swing upwardly by centrifugal force when shaft 11 is rotated. As illustrated in FIG. 10, the solids container 111 is rotated in the direction indicated by the arrow F directly into the fluid flow 112 to provide for maximum fluid solid interchange when finely divided solids are used. The solid container may also be attached to the rotor arms 16 and 17.

FIG. 13 discloses another alternate arrangement for measuring the angular displacement of rotor 13 in a centrifugic mass analyzer. As illustrated in FIG. 13, the rotating shaft 11 is powered by means of a magnetic drive motor 12 to rotate baskets 14 and 15 about a first axis of rotation A-A'. The shaft 11 is secured by a thrust bearing 135 and the autoclave chamber is sealed at 136 and 136a to prevent the escape of high temperature, high pressure gas. The gas may be admitted into the autoclave 40 by means of inlet 61 and exhausted through conduit 62 as has been previously described with respect to FIG. 2. A cooling chamber 136 is provided to insulate the autoclave from the driving and support mechanisms.

In the device illustrated in FIG. 13, an optical readout means is provided wherein a light source or any other radiant energy source 137 is positioned directly above rotor 13 and projects a beam of radiant energy 138 downwardly along axis A-A' through a quartz lens 144. An optical reflector means 139 is formed in rotor 13 to substantially deflect the beam of light or radiant energy from axis A-A' to a perpendicular axis indicated at 140. A quartz window 141 is provided in the wall of autoclave 40 with a series of photodiodes or other radiant energy responsive devices 142 arranged on the exterior of the autoclave chamber adjacent the quartz window. During operation of the device, the angular rotation of disc 13 causes a vertical displacement H-H' of the beam of radiant energy 140. As the beam or light ray sweeps past the quartz window 141, it energizes one of the photodiodes or other light sensitive devices 142 arranged on the exterior of the autoclave. The area energized is then converted into a measurement indicative of the angular displacement of rotor 13 by display device 143. Alternately, the value of the change in mass for the sample and container 14 may be calculated and displayed.

An alternate placement for light source 137 is indicated by dotted lines 137a in FIG. 13 wherein the light beam or beam of radiant energy is projected downwardly through a quartz lens 144a into the autoclave chamber 40. A portion of the support arm 16 designated at 145 is provided with a reflective device to reflect the light beam 138a through the quartz window 141 to strike the photodiode array at 142a. In this embodiment, an alternate compensating weight is added at 146 on the support arm 17. In each case, the device generates a single pulse of light on the photodiode array 142 for each revolution of shaft 11. The angular displacement of the beams 140 and 140a provide a derivative value of the change in mass in $M_s$ as the sample is subjected to preselected temperature and fluid variables.

Figure 15:
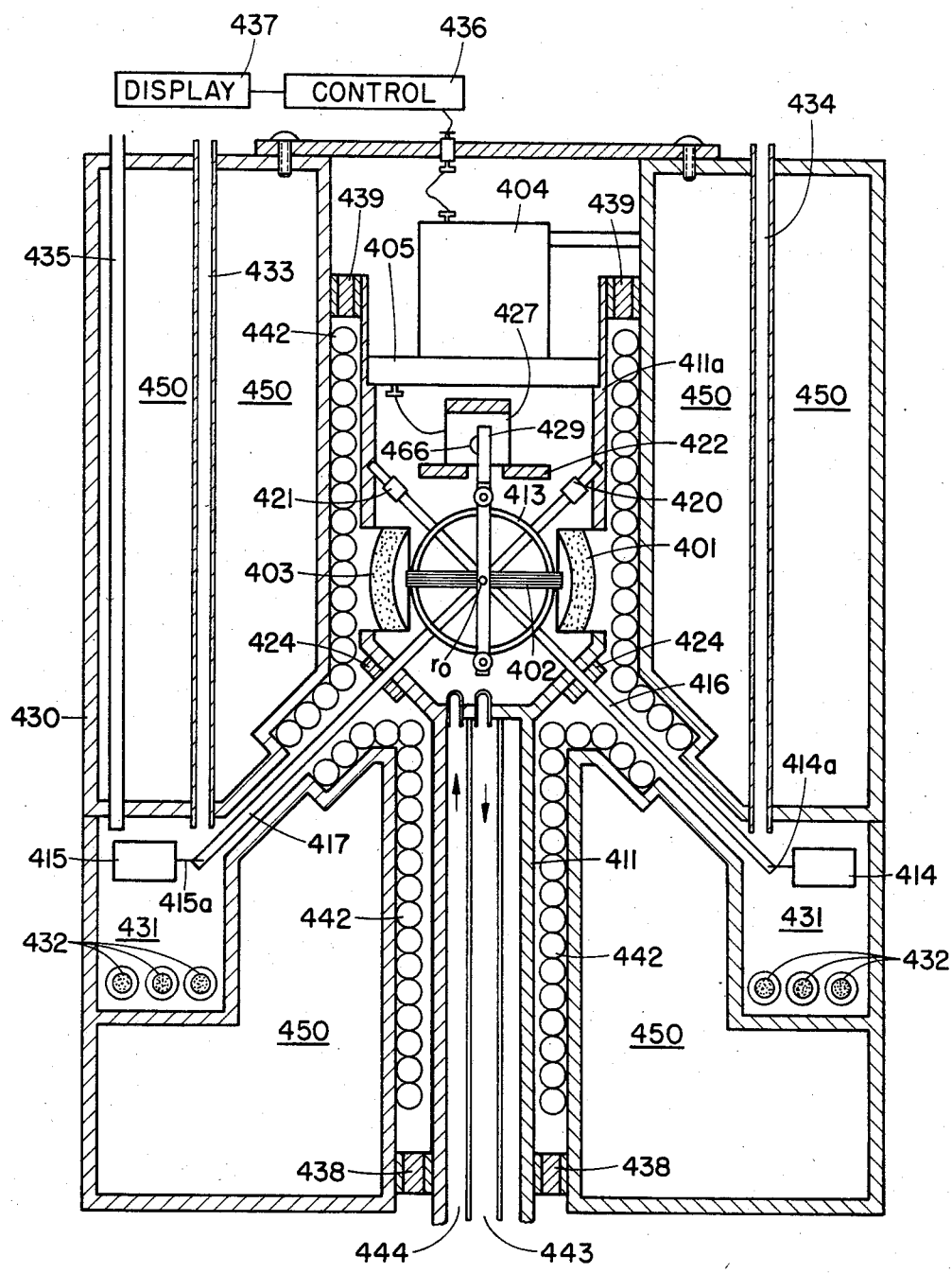
FIG. 15 is a cross-sectional view illustrating the use of the embodiment illustrated in FIG. 3 in an extremely high temperature autoclave.

FIGS. 15 and 16 illustrate the use of the embodiments previously described with respect to FIG. 3 and 8 and a high temperature autoclave environment. Both devices are "null" type devices involving very little angular displacement of the rotors inasmuch as any angular displacement is immediately compensated for by a compensating restoring force.

As illustrated in FIG. 15, a high temperature autoclave 430 is constructed with an annular autoclave chamber 431 which is heated by means of electric heating coils 432. For extremely high temperature applications the container hangers 414a, 415a may be extended for increased thermal insolation of the the gas chamber 431. In addition, if desired, the electrical heating means 432 may be replaced by an externally mounted radiation heating means with its thermal radiation focused along the circulation path of the container 414. The autoclave chamber is also supplied with a gas or fluid inlet conduit 433, and a gas or fluid outlet conduit 434. A thermocouple well 435 extends from above the cabinet 430 into the annular reaction chamber 431.

As was indicated previously with respect to FIG. 3, shaft 411 rotates rapidly with a reference weight $M_r$ in basket 415 and a sample $M_s$ in basket 414. Compensator weights 420 and 421 compensate for the rotor and provide rotor balance calibration weights. The rotor 413 rotates about $r_o$ upon a change in mass in $M_s$ carried by basket 414. This rotation is detected by means of photosensor 466 carried within transducer 427, as flag 429 moves from its center nulled position. As the photo-sensor 466 generates a control signal, the control signal is passed by means of rotating slip ring commutator 405 to the stationary slip ring commutator 404 to the control circuitry illustrated at 436. The control circuitry then energizes either coil 402 or 403, or both to generate a restoring force to return rotor 413 to its central nulled position wherein each of the arms 416 and 417 are equally aligned along the axis of rotation of shaft 411. Shaft 411 is journaled for rotation bearings 438-439 to provide for high speed rotation of the rotor arms 416 and 417. As was indicated previously with respect to FIG. 1, the speed of rotation may be several thousand rpm. In addition, the temperatures generated in the high temperature autoclave may be as high as 2,500 degrees. Cooling coils generally illustrated at 442 totally surround shaft 411 and 411a, and rotor 413 to insulate and cool the operating structure from the intense temperatures generated in the autoclave chamber 431. In addition, the reflective and insulated means 424 previously described with respect to FIG. 6, radiate the heat back towards the annular autoclave chamber 431. In addition to the coolant circulated through the coils 442, the shaft 411 may be cooled from the interior by means of coaxial conduits 443 and 444. In this embodiment, the annular conduit 444 provides a coolant inlet, while the center conduit 443 provides an outlet for the coolant.

The amount of current supplied to coil 402 and/or coil 403 to restore rotor 413 to a centered null position is then converted to a numerical display at 437 that may provide an indication of the change of weight in $M_s$ as it is reacted with the gaseous or fluid medium in the high temperature autoclave 431. The display for 437 may be an absolute or a functional value as desired.

The remainder of the interior within cabinet 430 is filled with insulation as indicated at 450.

The application of the "null" balance beam device to a high temperature autoclave environment is illustrated in FIG. 16. An autoclave cabinet 530 is used to house an annular high temperature autoclave chamber 531, and provides support bearings 538-539 for the rotating shaft 511. Rotating shaft also has support vanes 562 and 563 and an angularly displaceable arm 519 which rotates about pivot point 564 in the same manner as was described with respect to FIG. 7. The angular displacement of arm 519 caused by a change in $M_s$ placed in basket 514 is translated into vertical, reciprocal movement of reciprocating shaft 520. The vertical force is translated by means of platter 524 to the balance beam 521 in the same manner as was previously described with respect to FIG. 7. The control apparatus for FIG. 16 is the same as was illustrated with respect to FIG. 8. A null balance is preferred for the high temperature autoclave, inasmuch as it is desired to isolate the high temperature autoclave chamber 531 from the instrumentation chamber 570 as much as possible. For extremely high temperature applications the container hanger 514a may be significantly extended for increased thermal isolation. As was previously indicated with respect to FIG. 8, the balance beam 521 exerts a counter force on reciprocating shaft 520 to maintain the arm 519 in a constant angular displacement. Forces acting on balance beam 521 may be generated by the null point gravimetric balance device 550, the compression type null device 552, a rotational motor 551, or a linearly adjustable weight 544. The displacement of the balance beam 521 may be measured by the transducer 527 with respect to the metal or magnetic chip 529, or by the rotation of a rotational transducer 551 that measures the rotation of balance beam 521 about axis 526. As was previously indicated with respect to FIG. 8, electric, hydraulic or pneumatic devices may be used to generate the various forces on balance beam 521. Attached to vanes 562 and 563 are radiation shields 571 and 572 which may also be configured to provide maximum agitation of the gas or fluid in the high temperature autoclave chamber 531. High temperature fluid or gas is emitted through inlet port 533 and exited through exit port 534 during the reaction study. Or if desired, a given amount of reaction product may be introduced into the chamber 531, and the ports 533 and 534 sealed for the reaction. If desired, the rotating shaft 511 and the instrumentation chamber 570 may be insulated by cooling coils as was previously illustrated with respect to FIG. 15. The remainder of the chambers, however, is filled with insulation 550. If desired, the balance beam device illustrated in FIG. 16 may also be equipped with a conventional gravimetric scale 583 which is attached to balance beam 521 by means of cable 584 which passes through ports 580 and 581 and tubular member 582.

While the foregoing application has described a process and four distinctly separate mechanical devices for carrying out the process substantial variations in the details of the specific embodiments it should be apparent that the teaching and disclosure of the present invention will suggest other embodiments and variations to those skilled in the art. Many mechanical, optical, electrical, and electromechanical transducer devices are present that could be readily adapted or modified for the present invention to provide indication of the angular rotation of the rotor means 13, or the angular force generated by the rotor means in the null motor apparatus or the beam balance apparatus. One specific set of calculations has been included for test apparatus constructed and used in the determination of the change in mass of a test specimen subjected to elevated temperatures. The inclusion of the formulas as herein is not intended in any way to claim or restrict the use of the mathematical formula to applicant's invention, but is intended to teach those skilled in the art how to use applicant's invention to design centrifugometric mass analyzers capable of handling a variety of solid sizes in a variety of ambient operating conditions.

I claim:

1. A method for measuring the change in mass of a test sample when said sample is subjected to at least one selected temperature and fluid, said process comprising:
    a. balancing a test sample against a known reactive force, said sample being suspended in a angularly displaceable sample receiving means,
    b. rotating said sample receiving means about a first axis to amplify the apparent mass of the sample by centrifugal force,
    c. subjecting the test sample to at least one selected temperature and fluid,
    d. measuring the mass change of the sample, the mass change being derivative value of an angular displacement force about a second axis of rotation, said force being generated by the test sample as it is subjected to said centrifugal force and said selected temperature and fluid.

2. A method as claimed in claim 1, including the step of measuring an angular displacement about said second axis, whereby the change in mass of said tested sample may be measured by a derivative value of the angular displacement about the second axis.

3. A method as claimed in claim 1, including the step of generating a reactive force to balance the displacement force generated by said rotating test sample.

4. A method as claimed in claim 1, including the step of generating a compensating force to compensate for the apparent mass of the sample receiving means.

5. A method as claimed in claim 2 or 4, including the step of balancing a known reference mass against said test sample to balance the angular displacement of the test before the test sample is subjected to said rotation and selected temperature and fluid.

6. A method as claimed in claim 1 or 2 or 3 or 4, including the step of directing a high velocity fluid across the test sample as it is rotated.

7. A method as claimed in claim 1 or 2 or 3 or 4, including the step of rotating the sample receiving means between 200 rpm and 500 rpm.

8. A method as claimed in claim 1 or 2 or 3 or 4, including the steps of:
    a. rotating the sample at a speed of at least 200 rpm;
    b. elevating the temperature of the ambient atmosphere surrounding the sample to a preselected temperature.

9. A method as claimed in claim 1 or 2 or 3 or 4, which further includes a step of:
    a. rotating the sample at a speed of at least 200 rpm;
    b. surrounding said sample with a high pressure gaseous fluid at preselected temperatures.

10. A thermocentrifugometric analyzer for measuring the continuous mass change of a test material subjected to at least one selected temperature and fluid, said analyzer comprising:
    a. a rotating shaft and means for rotating said shaft around a first axis of rotation;
    b. a support means rotatable mounted on said shaft for rotation about a second axis of rotation, said second axis of rotation being perpendicular to said first axis of rotation;
    c. a test material holding means extending outwardly from said support means to support a test material while it is rotated about said first axis of rotation;
    d. a reference material holding means extending outwardly from said support means to support a know reference material while it is rotated about said first axis of rotation;
    e. enclosure means for subjecting the test material to at least one preselected temperature and fluid;
    f. means for measuring the angle of rotation of said support means about said second axis of rotation while said test material and said reference material are rotated about said first axis of rotation and subjected to said preselected temperature and fluid;
    whereby the change in mass of said tested material by be measured by a derivative value of said angle of rotation.

11. A thermocentrfugometric analyzer as claimed in claim 10, wherein said support means comprises a rotor; said sample holding means and said reference holding means being connected to said rotor by first and second outwardly extending arms.

12. A thermocentrifugometric analyzer as claimed in claim 10, wherein said analyzer further includes a compensator means mounted on said support means to compensate for the rotating mass of said support means and said sample holding means.

13. A thermocentrifugometric analyzer as claimed in claim 10, 11, or 12, wherein said enclosure means for subjecting said test material to at least one preselected temperature and fluid includes an autoclave enclosure having a heating means and means for admitting a preselected fluid.

14. A thermocentrifugometric analyzer as claimed in claim 10, 11 or 12 wherein said measuring means includes a beam of radiant energy.

15. A thermocentrifugometric analyzer as claimed in claim 14, wherein said support means further comprises a rotor with said sample holding means and said reference holding means connected to said rotor by first and second outwardly extending arms.

16. A thermocentrifugometric analyzer as claimed in claim 14, wherein said analyzer further includes a compensator means mounted on said support means to compensate for the rotating mass of said support means and said sample holding means.

17. A thermocentrifugometric analyzer as claimed in claim 10, therein said means for measuring the angle of rotation further includes a first rotating element within said enclosure, and a second rotating element mounted outside the enclosure responsive to the rotation of said first rotating element to indicate the angle of rotation.

18. A thermocentrifugometric analyzer as claimed in claim 17, wherein said measuring means includes an electronic transducer.

19. A thermocentrifugometric analyzer as claimed in claim 17, wherein said measuring means further includes an electronic transducer responsive to the rotation of said second rotating element.

20. A thermocentrifugometric analyzer for measuring the mass change of a test material subject to at least one selected temperature and fluid, said analyzer comprising:
    a. a rotatable means and means for rotating said means around a first axis of rotation;
    b. a rotor means rotatably mounted on said rotable means for rotation about a second axis of rotation perpendicular to said first axis of rotation;
    c. a test sample holding means extending outwardly from said support means to support a test material while it is rotated about said first axis of rotation;
    d. a reference material holding means extending outwardly from said support means to support a known reference material while it is rotated about said first axis of rotation;
    e. enclosure means for subjecting the test material to at least one preselected temperature and fluid;
    f. null motor means connected to said rotor means to generate a counter rotating force around said second axis of rotation to restore said support means to a null position;
    g. control means responsive to rotation of said rotor about said second axis to activate said null motor neans and restore said rotor to a null position about said second axis of rotation;

whereby the change in mass of said tested material by be measured as a derivative value of said counter rotational force applied by the null motor.

21. A thermocentrifugometric analyzer as claimed in claim 20, wherein said means for subjecting said test material to at least one preselected temperature and fluid include an autoclave enclosure having a heating means and means for admitting a preselected gaseous fluid.

22. A thermocentrifugometric analyzer for measuring the mass of a test material, said analyzer comprising:
    a. a rotating shaft and means for rotating said shaft about a first axis of rotation;
    b. support means mounted adjacent said rotating shaft for rotation about a second axis of rotation, said second axis of rotation being rotated to described a circumferential plane perpendicular to the axis of rotation of said rotating shaft;
    c. a sample receiving means for receiving said test material, said sample receiving means being mounted on said support means for angular rotation about a second axis of rotation as said support means is rotated about said first axis of rotation;
    d. means for biasing said sample receiving means to a preselected angular orientation with respect to the circumferential plane of said rotating support means;
    e. means for measuring the angular movement of said sample receiving means about said second axis of rotation as the mass of the test material is subjected to centrifugal force;

whereby the mass of said test material may be measured by a derivative value of said angular rotation.

23. A thermocentrifugometric analyzer as claimed in claim 22, wherein said analyzer further comprises:
    a. a reciprocal means for converting angular rotation about said second axis to reciprocal force along said first axis of rotation;
    b. a balance beam mounted across the reciprocal means to receive reciprocal force therefrom; whereby angular movement of the sample receiving means may be measured by said balance beam.

24. A thermocentrifugometric analyzer as claimed in claim 22, wherein including a balance beam for balancing said sample, said balancing bema comprising a coiled balance spring and an adjustable calibration weight.

25. A thermocentrifugometric analyzer as claimed in claim 22, 23, or 24 which further includes an enclosure means for subjecting the test material and the sample receiving means to at least one preselected temperature and fluid.

26. A thermocentrifugometric analyzer as claimed in claim 25, wherein said means for subjecting said test material to at least one preselected temperature and fluid include an autoclave enclosure having a heating means and means for admitting preselected gaseous fluids.

27. A thermocentrifugometric analyzer as claimed in claim 22, 23 or 24, wherein said support means is spaced from said rotating shaft by a radially extending blade member attached to said rotating shaft, said blade member having a first end rigidly affixed to said rotating shaft, and second end providing a pivot point for said support means whereby said rotating blade will agitate the fluid within an enclosure means therefore as said rotating shaft is rotated.

28. A thermocentrifugometric analyzer for measuring the mass of a test material, said analyzer comprising:
   a. a rotating shaft and means for rotating said shaft around a first axis of rotation;
   b. a support means rotatably mounted on said shaft for rotation about a second axis of rotation, said second axis of rotation being perpendicular to said first axis of rotation;
   c. a test material holding means extending outwardly from said support means to support a test material while it is rotated about said first axis of rotation;
   d. a reference material holding means extending outwardly from said support means to support a known reference material while it is rotated about said first axis of rotation;
   e. means for measuring the angle of rotation of said support means about said second axis of rotation when said test material and said reference material are rotated about said first axis of rotation;
   whereby the mass of said tested material may be measured by a derivative value of said angle of rotation.

29. A thermocentrifugometric analyzer as claimed in claim 28, wherein said support means comprises a rotor with said sample holding means and said reference holding means connected to said rotor by first and second outwardly extending arms.

30. A thermocentrifugometric analyzer as claimed in claim 28, which analyzer further includes compensator means mounted on said support means to compensate for the rotating mass of said support means and said sample holding means.

31. A method for measuring a change in mass of a test sample when the sample is subjected to at least one selected temperature and fluid, said process comprising:
   a. rotating a test sample about an axis to subject the sample to centrifugal force;
   b. subjecting the test sample to at least one selected temperature and fluid to effect a change in mass of the test sample;
   c. measuring a displacement force generated about a second axis during the rotation of the test sample about the first axis to determine a change in mass during an interval of time;
   whereby any change in mass in the test sample may be measured by a derivative value of the displacement forces generated at the beginning and end of said time interval.

32. A method for measuring a change in mass of a test sample as claimed in claim 31 wherein the sample is displaceable about said second axis and the displacement of the rotating test sample is measured to obtain a derivative value of the sample.

33. A method for measuring a change in mass of a test sample as claimed in claim 31, wherein the displacement force generated by the rotating test sample is measured to obtain a derivative value of the mass of the sample.

34. A method for measuring a change in mass of a test sample as claimed in claim 32 whereinthe displacement of the rotating test sample is converted to reciprocating movement.

35. A method for measuring a change in mass of a test sample as claimed in claim 34 wherein the reciprocating movement is measured by a balance beam.

36. A methed for measuring a change in mass of a test sample as claimed in claim 35 wherein the balance beam is initially balanced with reference weights to offset the force generated by the rotating test sample.

37. A method for measuring a change in mass of a test sample as claimed in claim 35 wherein the movement of the balance beam is measured by one or more transducers to generate a signal indicative of the change in mass of the test sample.

38. A method for measuring a change in mass of a test sample as claimed in claim 33 wherein the displacement force generated is transmitted to a balance beam and nulled by a null motor.

39. A method for measuring a change in mass of a test sample as claimed in claim 38 wherein the force generated by the null motor is measured to generate a signal indicative of the change in mass of the test sample.

40. A thermocentrifugometric analyzer for measuring the mass change of a test material subjected to at least one selected temperature and fluid, said analyzer comprising:
   a. a rotating shaft and means for rotating said shaft around a first axis of rotation;
   b. a test material holding means extending outwardly from said shaft to hold a test material while it is rotated about said axis of rotation, said holding means being rotatable about a second axis of rotation;
   c. an enclosure means for subjecting the test material to preselected temperature and fluid variables to effect a change of mass of said sample;
   d. means for measuring a displacement force generated by said test material holding means about said second axis when said test material is rotated about said axis of rotation and is subjected to at least one selected temperature and fluid.

41. A thermocentrifugometric analyzer for measuring the mass change of a test material as claimed in claim 40 including means for measuring the displacement of the test sample which comprises a means for converting said displacement about said second axis to reciprocal motion.

42. A thermocentrifugometric analyzer for measuring the mass change of a test material as claimed in claim 41 wherein the means for measuring the displacement force generated by the test sample is a balance beam.

43. A thermocentrifugometric analyzer for measuring the mass change of a test material as claimed in claim 42 which further includes reference weights for balancing said balance beam to thereby offset the force generated by the rotating test sample.

44. A thermocentrifugometric analyzer for measuring the mass change of a test material as claimed in claim 42 in which further includes one or more transducers for measuring the displacement of the balance beam to thereby generate a signal indicative of a change in mass of the test material.

45. A thermocentrifugometric analyzer for measuring the mass change of a test material as claimed in claim 40 wherein said means for measuring a displacement force further includes a balance beam and a null motor.

46. A thermocentrifugometric analyzer as claimed in claim 45 wherein said means for measuring a displacement force further includes an electrical circuit for measuring the force generated by said null motor.

47. A thermocentrifugometric analyzer for measuring the mass change of a test material, said analyzer comprising:
   a. a rotatable support means and drive means for rotating said support means about a first axis of rotation;

b. a null motor mounted on said support means, said null motor having a rotor describing a second axis of rotation perpendicular to said first axis;

c. test material holding means mounted on said rotor and extending outwardly from said first axis of rotation;

d. control means for detecting angular rotation about said second axis and energizing said null motor to return said rotor and test material holding means to a predetermined nulled position;

e. means for measuring the mass change of said test material said means responsive to a drive current supplied to said null motor by said control means to determine the mass change.

48. A thermocentrifugometric analyzer as claimed in claim 47 wherein said analyzer further includes a reference material holding means extending outwardly from said first axis of rotation.

49. A thermocentrifugometric analyzer as claimed in claim 47 or 48 wherein said analyzer further includes an enclosure surrounding the rotational path of said test material, and means for elevating the temperature of a fluid surrounding the test sample to a predetermined temperature.

* * * * *

UNITED STATES PATENT AND TRADEMARK OFFICE
CERTIFICATE OF CORRECTION

PATENT NO. : 4,596,470

DATED : June 24, 1986

INVENTOR(S) : Jin Y. Park

It is certified that error appears in the above-identified patent and that said Letters Patent is hereby corrected as shown below:

In the Abstract, line 4: "apply" should read as --amplify--

Column 2, line 50: after "suspended" insert --particle with a diameter greater than one inch. It is not--

Column 3, line 6: "closes" should read as --discloses--

Column 13, line 1: "Thys" should read as --Thus--

Column 27, line 53, Claim 20: "support" should read as --rotor--

Column 27, line 56, Claim 20: "support" should read as --rotor--

Column 27, line 63, Claim 20: "support" should read as --rotor--

Column 27, line 67, Claim 20: after "rotor" insert --means--

Column 27, line 67, Claim 20: "neans" should read as --means--

Signed and Sealed this

Fourth Day of August, 1992

*Attest:*

DOUGLAS B. COMER

*Attesting Officer*      *Acting Commissioner of Patents and Trademarks*